United States Patent [19]

Green et al.

[11] Patent Number: 5,645,551

[45] Date of Patent: *Jul. 8, 1997

[54] APPARATUS AND METHOD FOR APPLYING SURGICAL CLIPS

[75] Inventors: David T. Green, Westport; Henry Bolanos, East Norwalk, both of Conn.; Wayne P. Young, Brewster, N.Y.; Richard A. McGarry, Norwalk, Conn.; Lisa W. Heaton, Norwalk, Conn.; Keith Ratcliff, Sandy Hook, Conn.

[73] Assignee: United States Surgical Corporation, Norwalk, Conn.

[*] Notice: The portion of the term of this patent subsequent to Jul. 18, 2009, has been disclaimed.

[21] Appl. No.: 300,254

[22] Filed: Sep. 2, 1994

Related U.S. Application Data

[63] Continuation of Ser. No. 860,650, Mar. 30, 1992, Pat. No. 5,423,834, which is a continuation of Ser. No. 381,265, Jul. 18, 1989, Pat. No. 5,100,420.

[51] Int. Cl.[6] .................................................. A61B 17/04
[52] U.S. Cl. ........................................................... 606/143
[58] Field of Search ..................................... 606/142, 143; 227/901

[56] References Cited

U.S. PATENT DOCUMENTS

| | | |
|---|---|---|
| 2,968,041 | 1/1961 | Skold . |
| 3,870,048 | 3/1975 | Yoon . |
| 3,955,581 | 5/1976 | Spasiano et al. . |
| 3,989,049 | 11/1976 | Yoon . |
| 4,085,743 | 4/1978 | Yoon . |
| 4,103,680 | 8/1978 | Yoon . |
| 4,152,920 | 5/1979 | Green . |
| 4,166,466 | 9/1979 | Jarvik . |
| 4,185,762 | 1/1980 | Froehlich . |
| 4,196,836 | 4/1980 | Brecht . |
| 4,226,239 | 10/1980 | Polk et al. . |
| 4,226,242 | 10/1980 | Jarvik . |
| 4,228,895 | 10/1980 | Larkin . |
| 4,230,116 | 10/1980 | Watson . |
| 4,242,902 | 1/1981 | Green . |
| 4,246,903 | 1/1981 | Larkin . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,372,316 | 2/1983 | Blake, III et al. . |
| 4,374,523 | 2/1983 | Yoon . |
| 4,412,539 | 11/1983 | Jarvik . |
| 4,425,915 | 1/1984 | Ivanov . |
| 4,430,997 | 2/1984 | DiGiovanni et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,471,781 | 9/1984 | Di Giovanni et al. . |
| 4,492,232 | 1/1985 | Green . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,556,058 | 12/1985 | Green . |
| 4,557,263 | 12/1985 | Green . |
| 4,562,839 | 1/1986 | Blake, III et al. . |
| 4,572,183 | 2/1986 | Juska . |
| 4,576,166 | 3/1986 | Montgomery et al. . |

(List continued on next page.)

*Primary Examiner*—Gary Jackson

[57] ABSTRACT

An apparatus for applying surgical clips through an endoscopic tube includes an endoscopic portion housing a jaw blade, a pusher bar for feeding clips one at a time to the jaws, a channel bar for camming the jaw blades into closed position, and an array of surgical clips. The body of the apparatus comprises a frame housing an actuating mechanism and a transmission mechanism for transferring movement to the pusher bar and channel. The endoscopic portion is rotatable relative Go the frame. In one embodiment the apparatus is a single disposable unit. In an alternative embodiment the endoscopic portion is detachable and disposable whereas the non-endoscopic body portion is reusable.

14 Claims, 27 Drawing Sheets

U.S. PATENT DOCUMENTS

| | | |
|---|---|---|
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. ............... 606/143 |
| 4,646,740 | 3/1987 | Peters et al. . |
| 4,662,373 | 5/1987 | Montgomery et al. ........... 606/143 |
| 4,662,374 | 5/1987 | Blake, III . |
| 4,674,504 | 6/1987 | Klieman et al. . |
| 4,691,853 | 9/1987 | Storace . |
| 4,712,549 | 12/1987 | Peters et al. . |
| 4,850,355 | 7/1989 | Brooks et al. . |
| 4,944,443 | 7/1990 | Oddsen et al. . |
| 5,030,226 | 9/1991 | Green et al. . |
| 5,049,152 | 9/1991 | Simon et al. . |
| 5,100,418 | 3/1992 | Yoon et al. . |

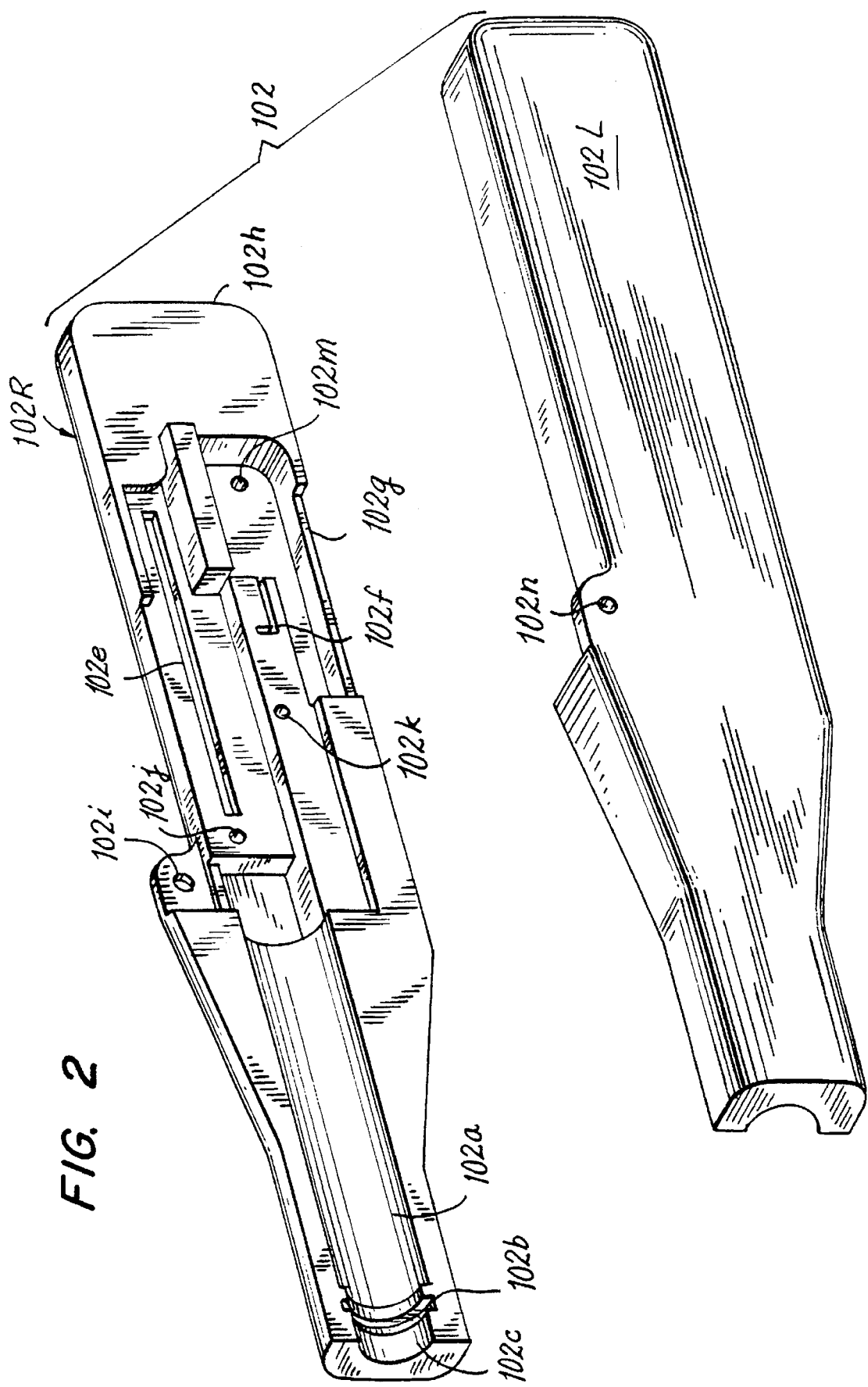

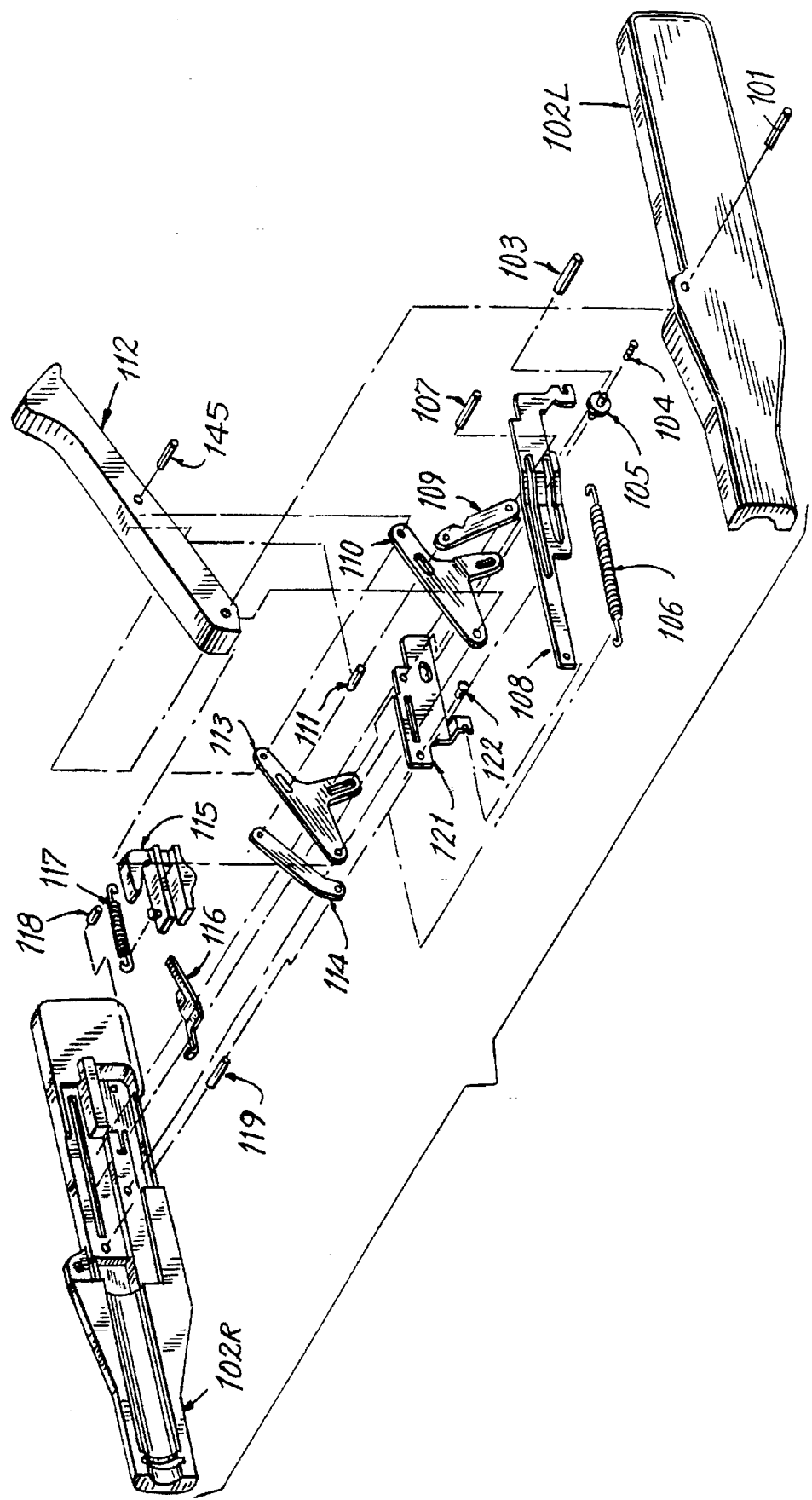

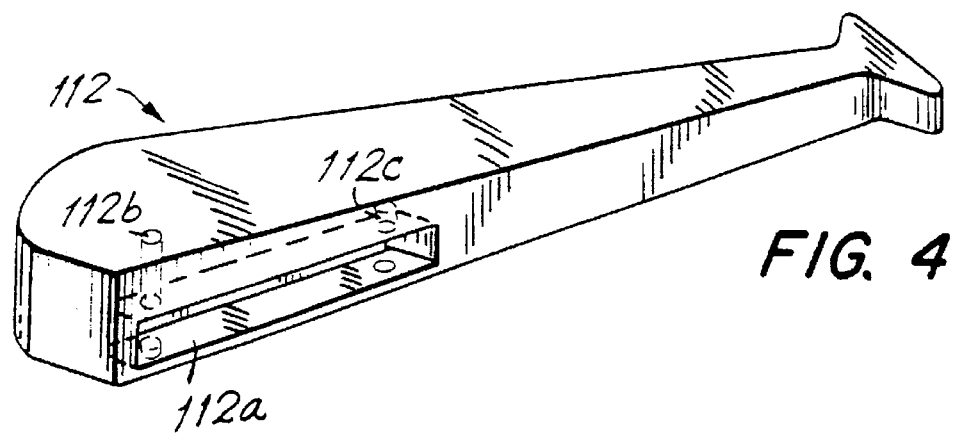
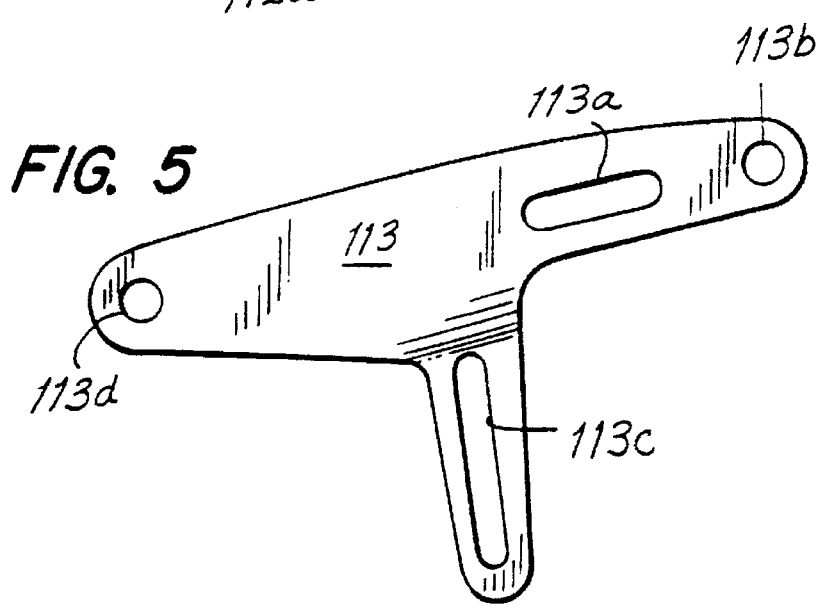
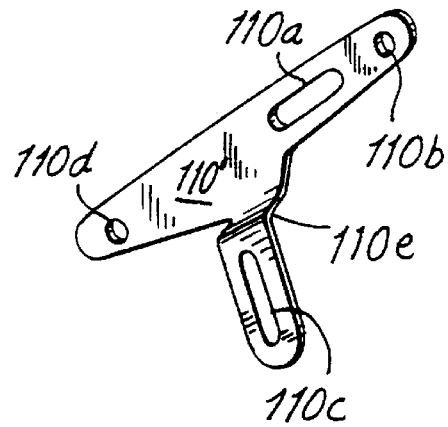
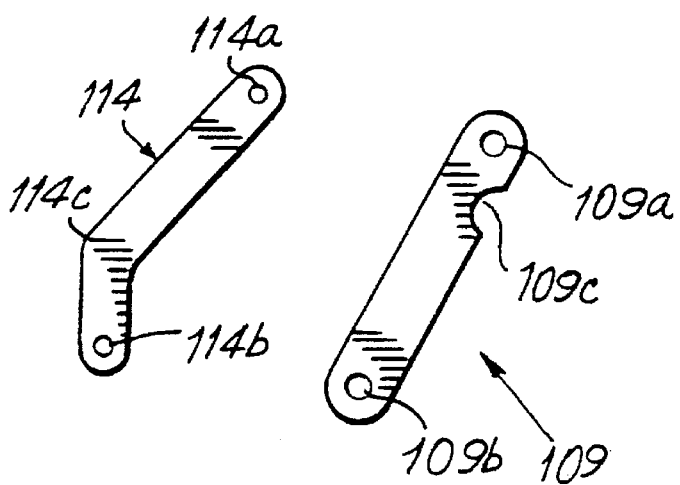
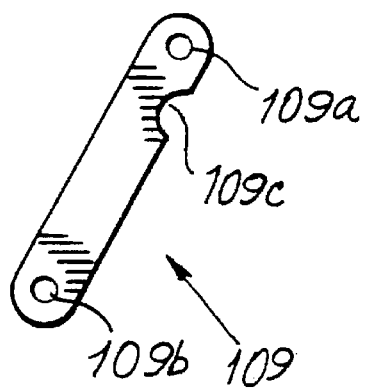

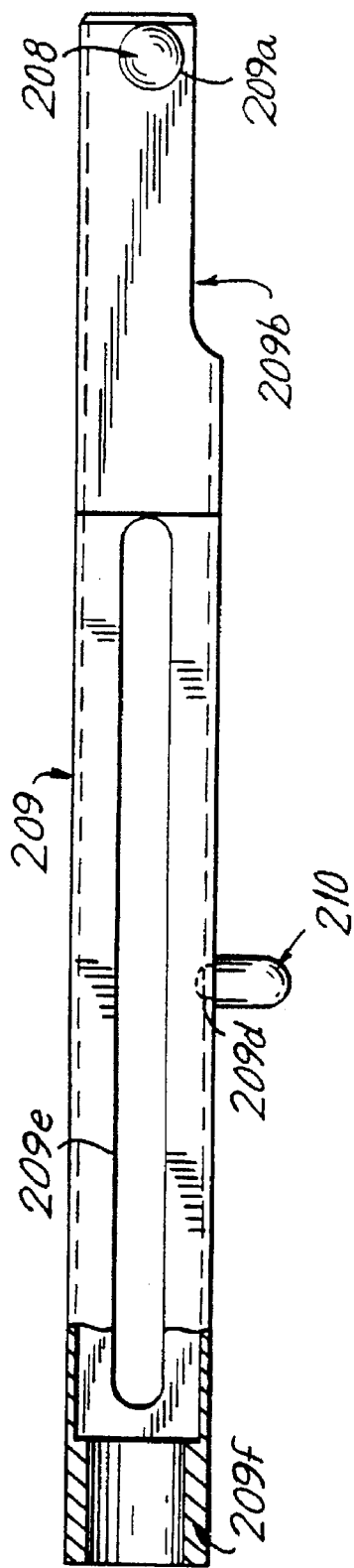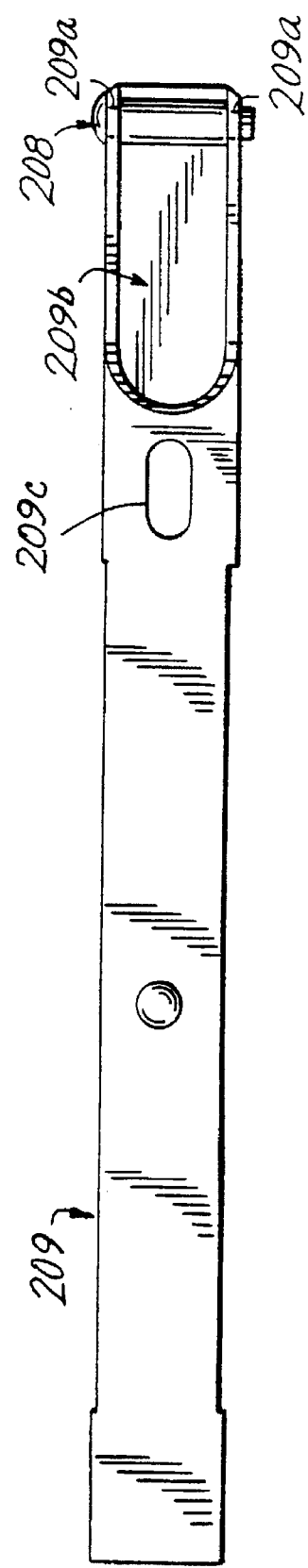
FIG. 24a
FIG. 24b

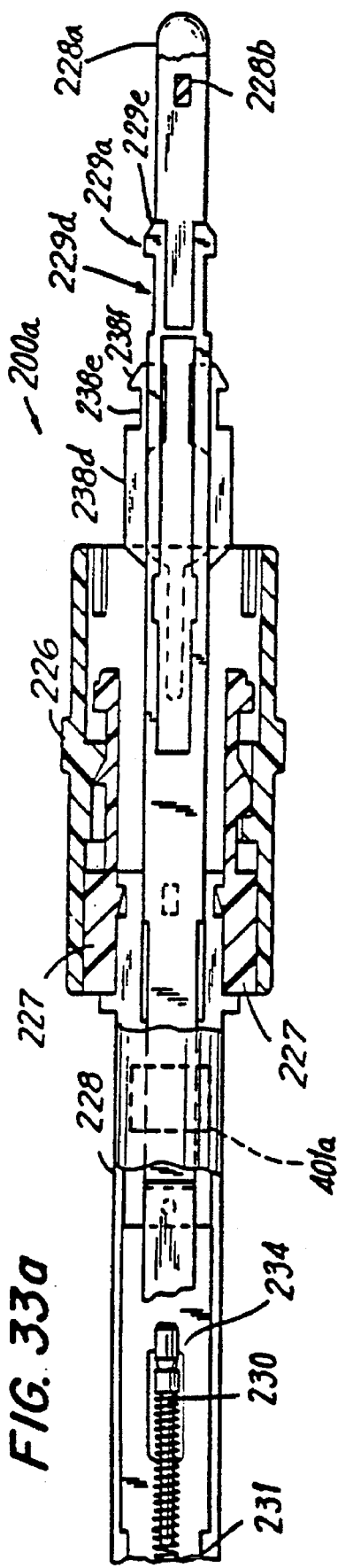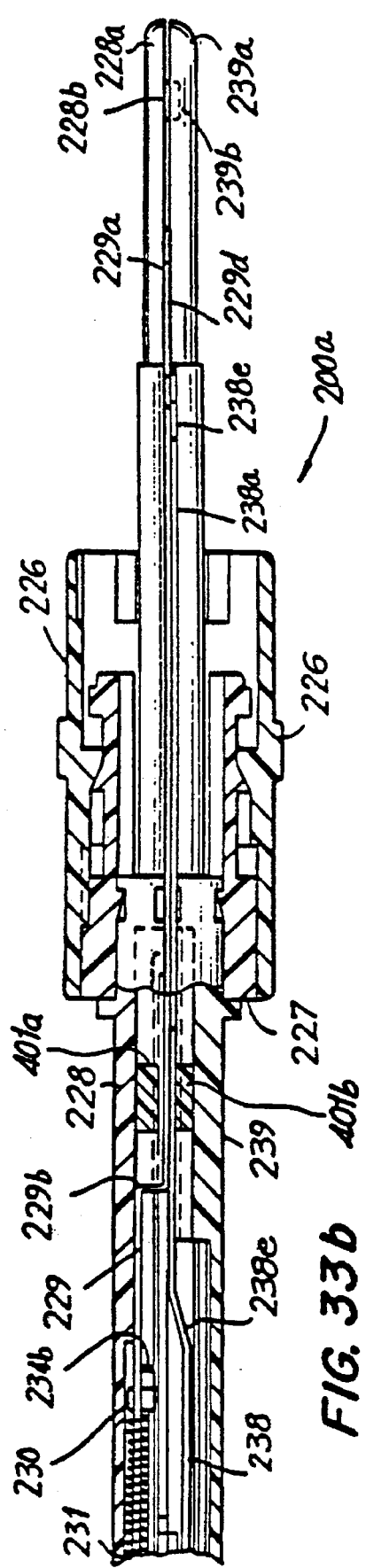
FIG. 33a
FIG. 33b

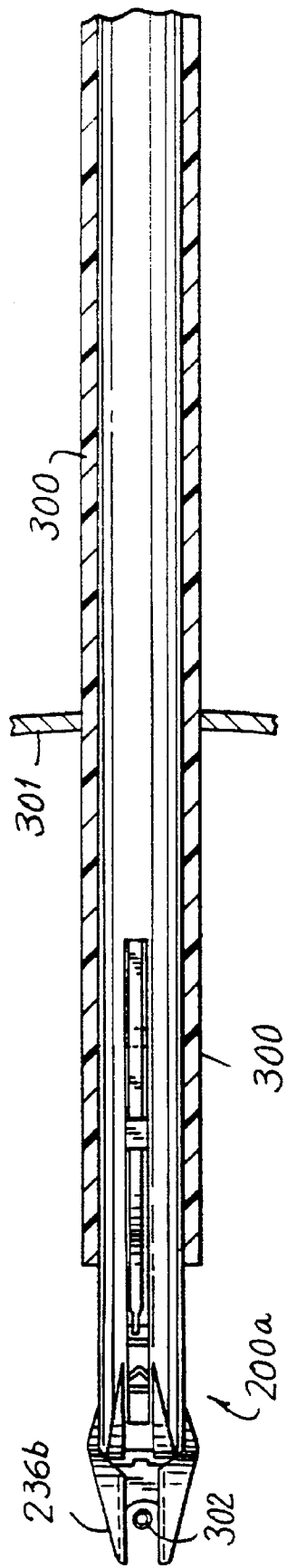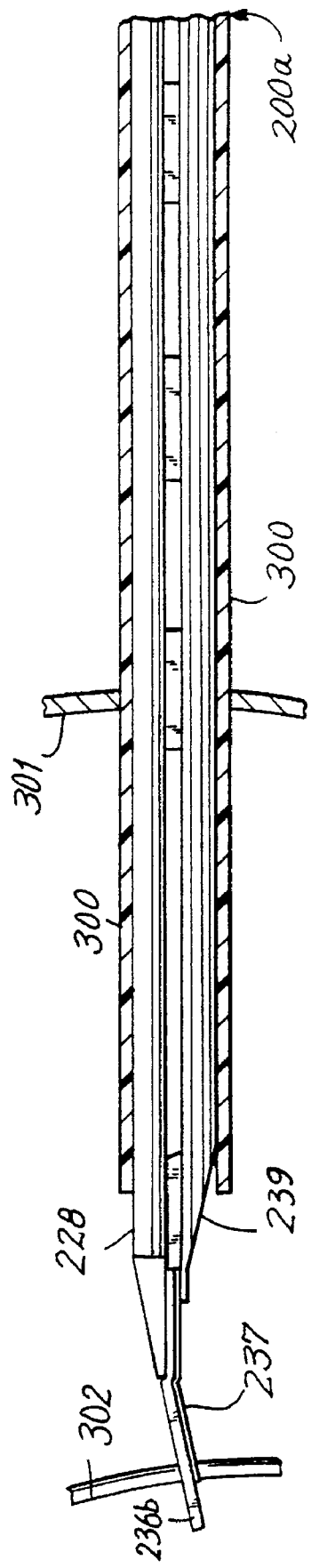

APPARATUS AND METHOD FOR APPLYING SURGICAL CLIPS

This is a continuation of application Ser. No. 07/860,650, filed on Mar. 30, 1992, which was a continuation of prior application Ser. No. 07/381,265, filed Jul. 18, 1989, now U.S. Pat. No. 5,100,420.

BACKGROUND OF THE INVENTION

1. Field of the Invention

This invention relates to an apparatus and method for applying surgical clips, especially hemostatic clips, to body tissue such as blood vessels. More particularly, this invention relates to a surgical clip applier which can be used in laparoscopic or endoscopic procedures, and a method for using same.

2. Background of the Related Art

In surgical operations it is often necessary to apply hemostatic clips to blood vessels, and apparatus for applying clips are known in the art. See, for example, U.S. Pat. No. 4,616,650, and 4,624,254, both of which are hereby incorporated by reference, which disclose a surgical clip applying apparatus having a pair of ring-like handles. The handles are squeezed to force jaws to move distally relative to the apparatus where they are forced together by a pair of inclined surfaces. A surgical clip between the jaws is thereby squeezed closed.

In laparoscopic procedures surgery is performed in the interior of the abdomen through a small incision; in endoscopic procedures surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments to be used in such procedures be both long and narrow. Up to now there have been no instruments for placing surgical clips in laparoscopic or endoscopic procedures.

Because endoscopic procedures are more common than laparoscopic procedures, the present invention shall be discussed in terms of endoscopic procedures and apparatus. However, use herein of terms such as "endoscopic", "endoscopically" and "endoscopic portion", among others, refer generally to instruments having elongated and relatively narrow operating portions for inserting into a cannula or a small wound in the skin and should not be construed to limit the present invention to an apparatus for applying surgical clips only in conjunction with an endoscopic tube. To the contrary, it is believed that the present invention may find use in any procedure where access is limited to a small incision, including, but not limited to laparoscopic procedures.

SUMMARY

In accordance with the present invention a surgical apparatus is provided for applying surgical clips to blood vessels or other body tissue.

Briefly, a clip applier of the present invention comprises
a) a frame,
b) an endoscopic portion defining a longitudinal axis and extending distally from said frame, said endoscopic portion comprising
   i) means for storing a plurality of surgical clips;
   ii) clip closing means including jaw means, and camming means for closing said jaw means;
   iii) means for individually advancing the surgical clips one at a time to said jaw means.

The ability to rotate the endoscopic portion independently from the body of the instrument greatly facilitates its use in endoscopic procedures. Further includable features are first transmission means for linearly transmitting movement along the axis of the apparatus from the actuating means to the clip closing means, and second transmission means for linearly transmitting movement along the axis of the apparatus from the actuating means to the means for feeding the surgical clips to the jaw means; and locking means for locking the apparatus such that once the jaw means have been actuated the apparatus cannot be reactivated until the locking means is released.

In one embodiment of the present invention the frame and endoscopic portion of the apparatus are not separable and the apparatus is intended to be completely disposable.

In another embodiment of the present invention the endoscopic portion is formed as a disposable unit detachable from a reusable frame and handle portion.

According to a method of the present invention the endoscopic portion of the apparatus is inserted into the body through a small incision or, more likely, through an endoscopic tube. The blood vessel or other tissue to be clipped is engaged by the jaws of the apparatus. A clip is positioned between the jaws and the jaws are closed, thereby applying the clip to the blood vessel.

The apparatus of the present invention advantageously permits a surgeon to perform internal clip application without full access to the operation site, i.e., without providing a large opening in the body to allow access to the operation site. The frame and handle portion of the apparatus are manipulated outside of the patient's body. Additionally the endoscopic portion may be rotated so as to facilitate positioning of the clip.

The ability to apply surgical clips through a small incision or tube dramatically reduces blood loss, tissue trauma, and patient recovery time, thereby contributing to improved health care practices.

BRIEF DESCRIPTION OF THE DRAWINGS

FIG. 2 illustrates a perspective view of the frame portions of the embodiment of FIG. 1;

FIG. 3 illustrates an exploded perspective view of the actuating mechanism of the embodiment of FIG. 1;

FIG. 4 illustrates a perspective view of the handle;

FIG. 5 illustrates a side view of the right toggle lever;

FIG. 6 illustrates a perspective view of the left toggle lever;

FIG. 7 illustrates a side view of the pusher bar front link;

FIG. 8 illustrates a side view of the pusher bar rear link;

FIGS. 24a and 24b illustrate in sectional side view and bottom view respectively, the pusher tube of an alternative embodiment;

FIGS. 33a and 33b illustrate the proximal section of the endoscopic portion of an alternative embodiment;

FIGS. 34a and 34b illustrate the endoscopic portion of the apparatus used in conjunction with the cannula of a trocar in top and side views, respectively;

DETAILED DESCRIPTION OF PREFERRED EMBODIMENTS

Figure 1:
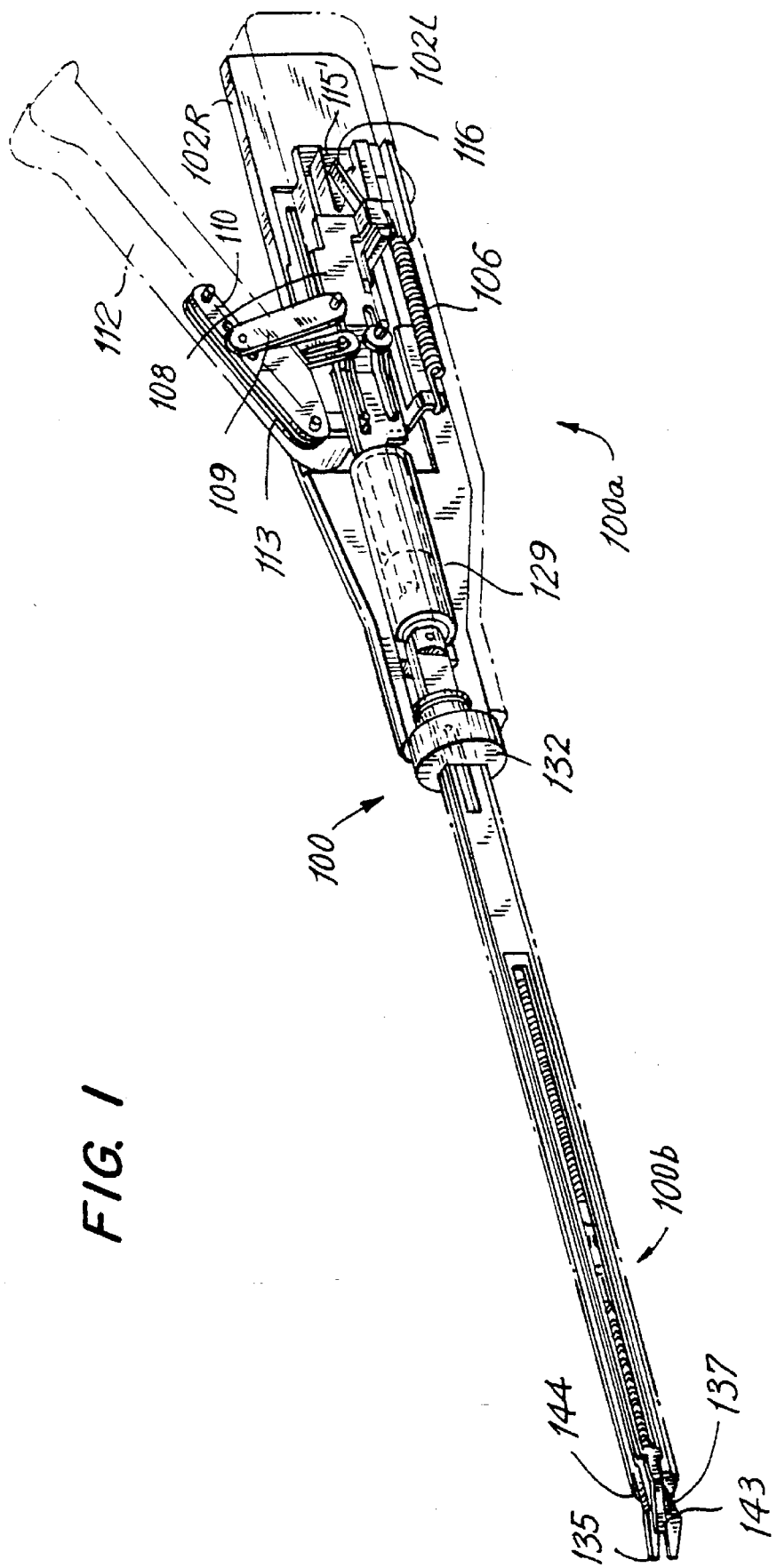
FIG. 1 illustrates a cutaway perspective view of one embodiment of the present invention.

The surgical apparatus described herein is adapted to apply surgical clips to blood vessels and the like, in endoscopic or laparoscopic procedures.

The apparatus or instrument generally comprises a frame which is of a size convenient for being held in the hand and which houses the non-endoscopic body of the apparatus. An endoscopic portion defining a longitudinal axis extends distally from the frame and is rotatable around the longitudinal axis relative to the frame. The endoscopic portion is a long tube-like portion having a relatively narrow outer diameter (e.g., about 10 millimeters) for insertion into an endoscopic tube such as a trocar cannula, or a small incision.

The endoscopic portion comprises means for holding a longitudinal array of surgical clips, such as a track, with a spring means to bias the clips forward in the distal direction. The clips are generally U-shaped pieces of integral construction and comprise two spaced apart legs connected by a bridge portion. The endoscopic portion has a clip closing means comprising a pair of flexible opposing jaws which are cammed together into closure by a distally-moving channel, and means such as a spring mounted pusher bar for advancing the surgical clips one at a time to the jaws.

The apparatus further has actuating means such as a pivoting handle and connecting links and levers which are part of a transmission means for transferring the pivotal movement of the actuating means linearly along the instrument axis to both the clip closing and clip advancing means. The apparatus also includes tubular members with circumferential coupling means such as circumferential notches or projections, which allow a connection of the endoscopic portion to the frame such that linear actuation movement may be transmitted thereto while allowing the endoscopic portion to rotate around the instrument axis.

The apparatus further comprises a locking means such that once the jaw means have been actuated and opened, the apparatus cannot be reactuated until the locking means is released, usually by a release button. The locking means comprises a resilient catch (such as a catch in conjunction with a spring) which is movable in response to actuation of the apparatus, i.e., application of a clip, from an unlocked position to a locked position. In the locked position, the locking means is engaged, thereby preventing linear transfer of movement to the clip closing means by the transmission means. Preferably two spring catches are used, one for locking the transmission means for actuating the clip advancing mechanism (e.g., pusher bar), and a second catch for locking the transmission means for actuating the jaw closing means (e.g., the channel). Pressing the release button releases both the first and second catches. The first catch is released directly thereby allowing the first transmission means to slide forward, and the second catch is released in response to the forward movement of the first transmission means.

As mentioned above, endoscopic instrumentation is usually required to have a gaseous seal to prevent communication of gases through the endoscopic incision. This gaseous seal may be accomplished in the apparatus of the present invention by providing close tolerances between the outer diameter of the endoscopic portion and the inner diameter of the trocar cannula through which it is inserted, and by providing close tolerances for the internal moving parts of the endoscopic portion. Thus adapted, the instrument of the present invention will provide a suitable gaseous seal.

Figure 35:
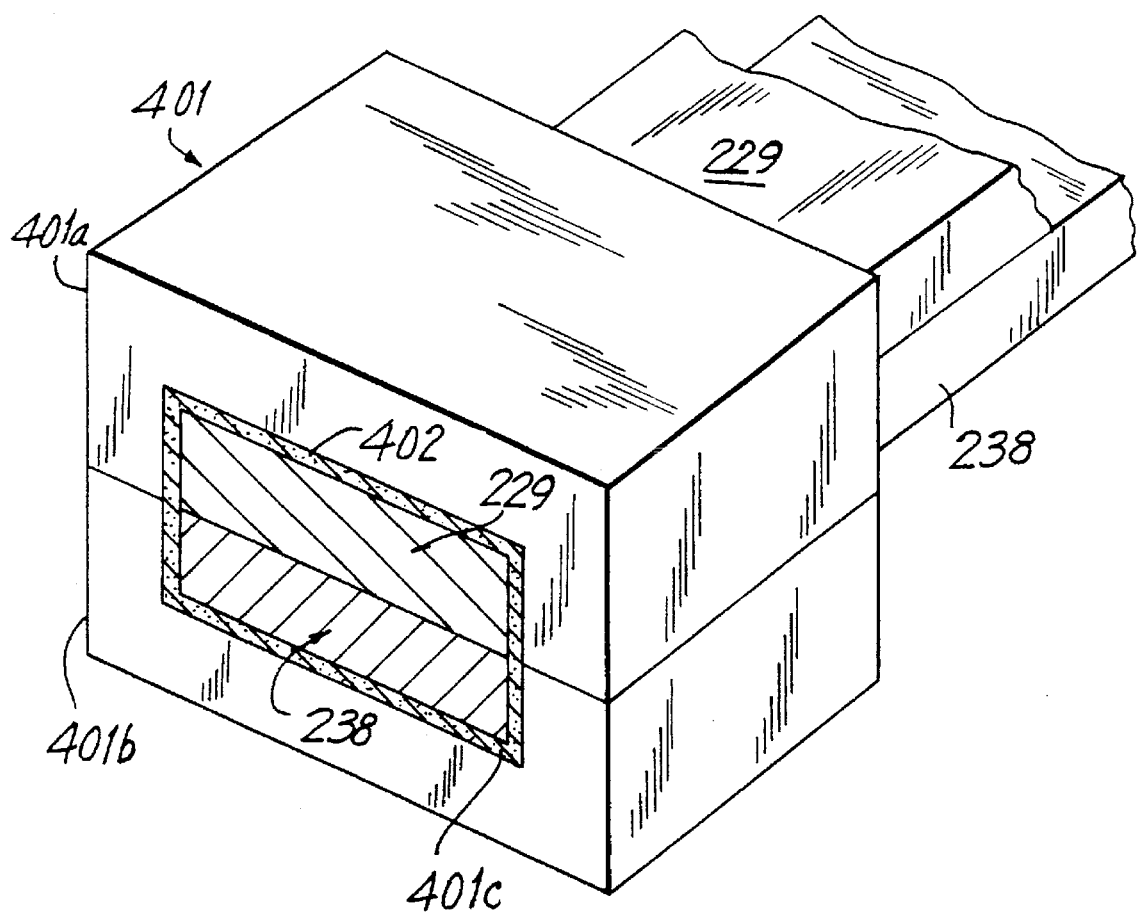
FIG. 35 illustrates the sealing block in perspective view.

Optimally, the gaseous sealing means comprise sealing block 401, as illustrated in FIG. 35. Sealing block 401 comprises U-shaped upper and lower portions 401a and 401b, respectively, which are positioned together so as to define an axially extending opening 401c through which components such as channel 238 and pusher 229 may be disposed. The inner surface of opening 401c is in close contiguity with the surface of the components disposed therethrough. A layer of silicone grease 402 may be employed to prevent gases from leaking between the surfaces. The sealing block 401 may be located within the cover tube 144 or the cartridge portions 228 and 239 of the embodiments disclosed herein. See, for example, FIGS. 18 and 29.

After the clipping operation has been completed the instrument may be removed from the body. In one embodiment of the present invention the entire instrument may be discarded. In another embodiment the endoscopic portion may be detached and discarded, and the frame and handle portion may be retained for a subsequent reuse with a replacement of the endoscopic portion.

FIG. 1 shows a cutaway perspective view of one embodiment of the present invention 100 which generally comprises an actuating body 100a supporting a non-detachable endoscopic portion 100b. Included are means for actuating the instrument, transmission means, means for applying a surgical clip to a blood vessel or the like, means for locking the instrument, and means for unlocking the instrument and repositioning another clip. Clip applier 100 is intended to be fully disposable.

More particularly, referring now to FIGS. 1 and 2, frame 102 comprises a left portion 102L and a right portion 102R. These portions are optimally fastened together by means of fastening screws, although rivets, welds, adhesives, or other means of joining the frame portions may be used. Frame 102 is elongated and has an interior surface defining a distal opening 102c, a proximal end 102h, an interior distal chamber 102a, a circumferential groove 102b, an upper guideway 102e to receive pins 107 and 103 (see below), a mounting slot 102f (to receive spring 116), elongated access aperture 102g, and pin mounting holes 102i, j, k, m and n for receiving pins 101, 119, 105, 118 and 101, respectively. The frame is of overall size and shape convenient for being held in the hand.

Referring additionally now to FIGS. 3, 4, 5, 6, 7 and 8, handle 112 is pivotally mounted to the frame 102 by means of handle pin 101 which is disposed through holes 102n and 102i in the frame, and hole 112b in the distal portion of the handle 112. Handle 112 also has an elongated cavity 12a for receiving the toggle levers 110 and 113. Hole 112c receives lever pin 145. Handle 112 serves as a means to activate the instrument when said handle is pivoted clockwise by the user of the instrument.

Toggle levers 113 and 110 are T-shaped levers which are pivotally mounted to the handle 112. Lever 113 has a proximal aperture 113b for receiving pin 145, a distal aperture 113d for receiving pin 101, said pins being respectively disposed through holes 112c and 112b in the handle 112. Lever 113 also has an elongated slot 113a for receiving pin 111, and a lower slot 113c for receiving pin 103.

Toggle lever 110 is similar to toggle lever 113 except that the lower portion is offset to the left by bend 110e. Slot 110c in the lower portion is for receiving pin 103. Slot 110a in the upper portion receives pin 111, and apertures 110b and 110d receive pins 145 and 101, respectively. The lower legs of the toggle levers 113 and 110 transmit motion of handle 112 to the rear channel 121 via pin 103.

Pusher bar rear link 109 is a flat elongated piece having an aperture 109a for receiving pin 111, an aperture 109b for receiving pin 107, and a curved notch 109c for accommodating pin 145 when the handle 112 is pushed down into a closed position. Pusher bar rear link 109 transfers movement from the handle 112 to the rear pusher bar 108.

Pusher bar front link 114 is an elongated flat piece having a bend 114c, aperture 114a for receiving pin 111, and aperture 114b for receiving pin 119.

Figure 9:
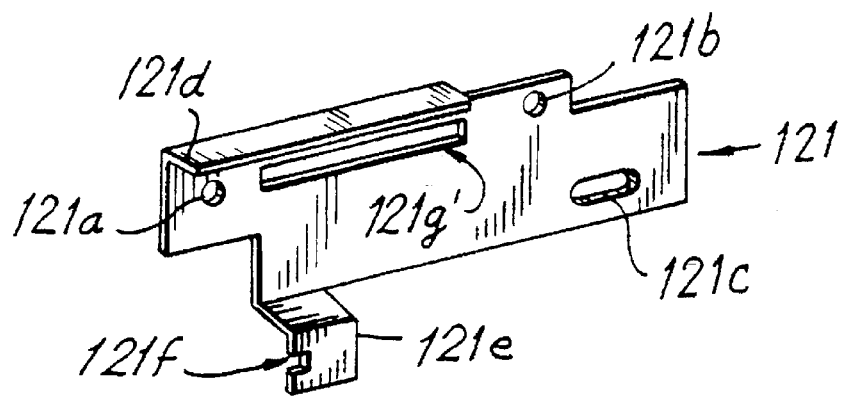
FIG. 9 illustrates a perspective view of the rear channel.
Figure 10:
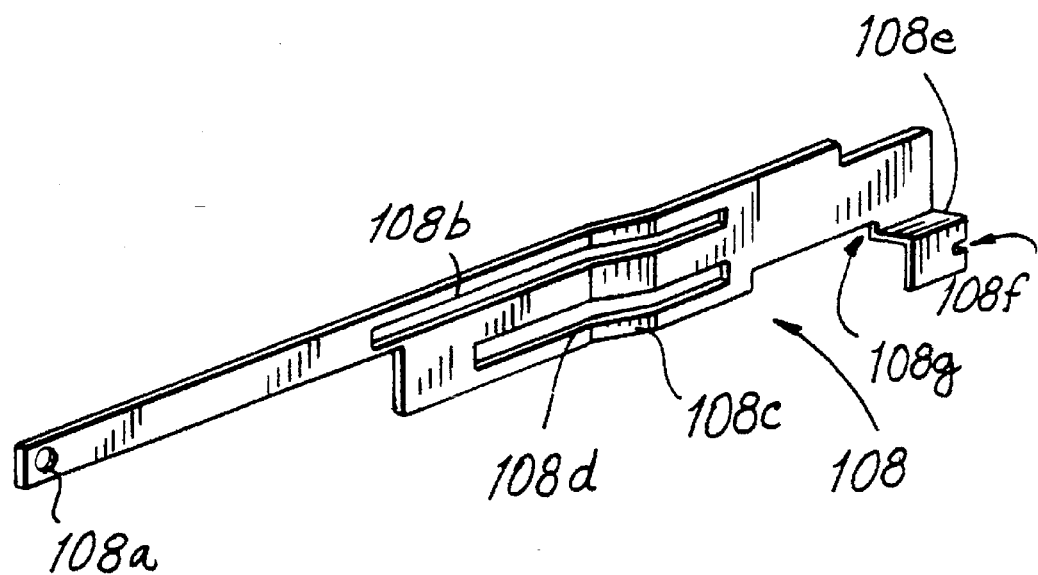
FIG. 10 illustrates a perspective view of the rear pusher bar.
Figure 15:
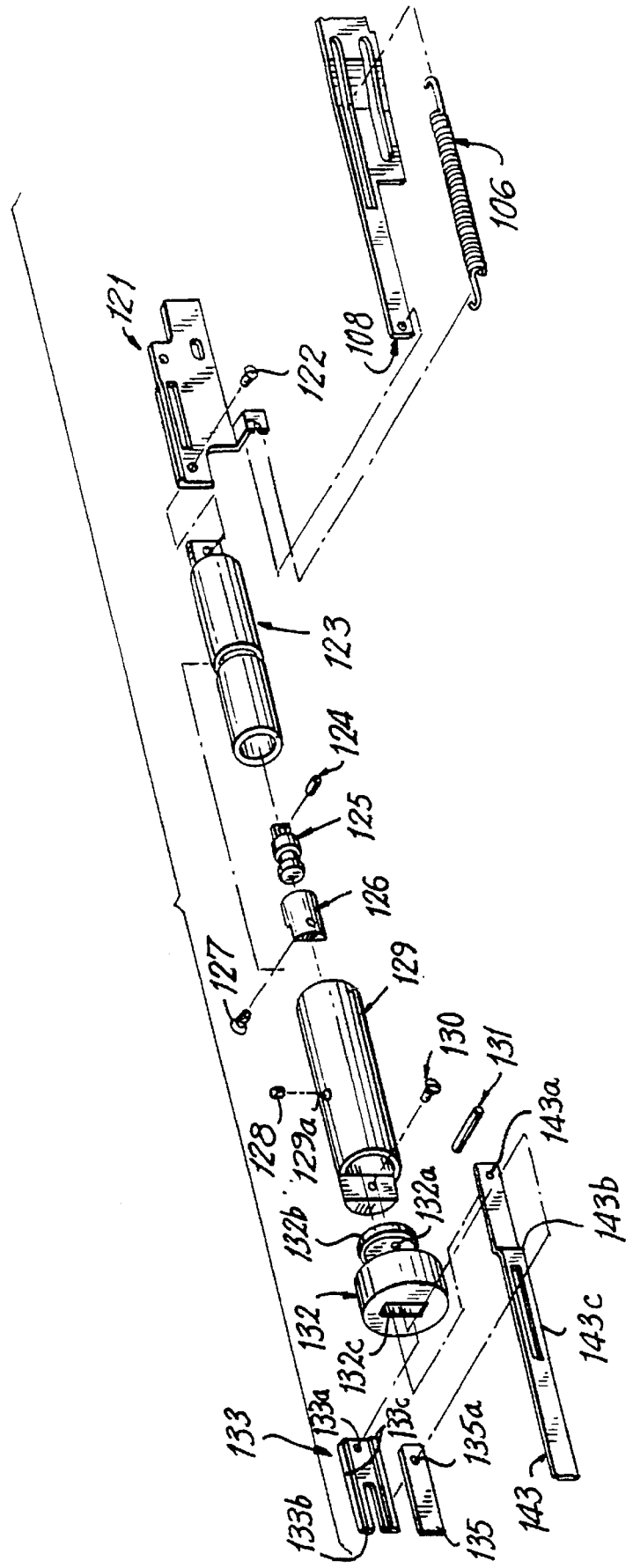
FIG. 15 illustrates an exploded perspective view of the transmission mechanism of the present invention.

Referring additionally now to FIGS. 9 and 10, rear channel 121 is longitudinally movable and has a distal aperture 121a to receive screw 122 for attachment to the rear channel tube 123 (see FIG. 15.). Rear channel 121 also has a proximal aperture 121b to receive pin 103. Slot 121g receives pin 119 and aperture 121c receives channel lock pin 105. Rear channel 121 has an overhang 121d, and a lower offset flap 121e with notch 121f for holding the distal end of spring 106. Rear channel 121 receives pivotal movement from toggle levers 110 and 113, and transfers motion linearly to the rear channel tube 123.

Rear pusher bar 108 is longitudinally movable and has a distal aperture 108a to receive pin 124 for mounting the distal end to the rear pusher bar tube 125 (see below). Rear pusher bar 108 also comprises upper slot 108b for receiving pin 119, lower slot 108d for receiving the channel lock pin 105, camming surface 108c, and offset flap 108e with proximal notch 108f for receiving the proximal end of spring 106. Rear pusher bar 108 further possesses a stopping edge 108g which provides a catch means for engaging the locking flap of the pusher bar stop spring 116 (see below). Rear pusher bar 108 provides means for transferring pivotal movement from link 109 linearly to rear pusher bar tube 125.

Figure 11:
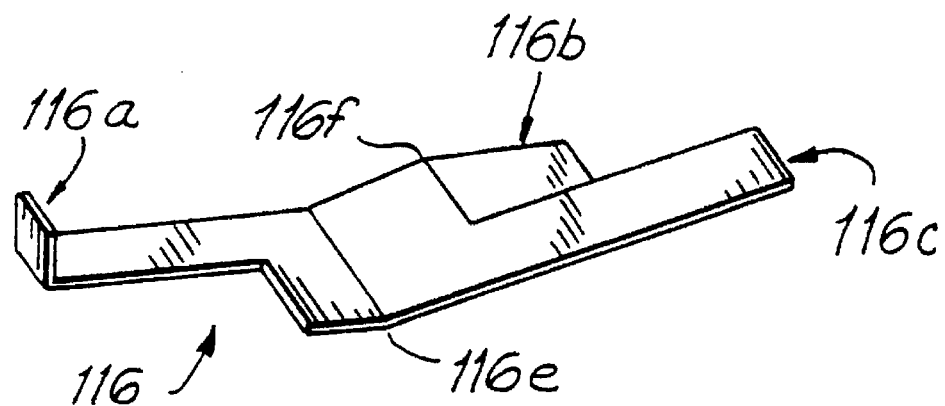
FIG. 11 illustrates a perspective view of the pusher bar stop spring.
Figure 12:
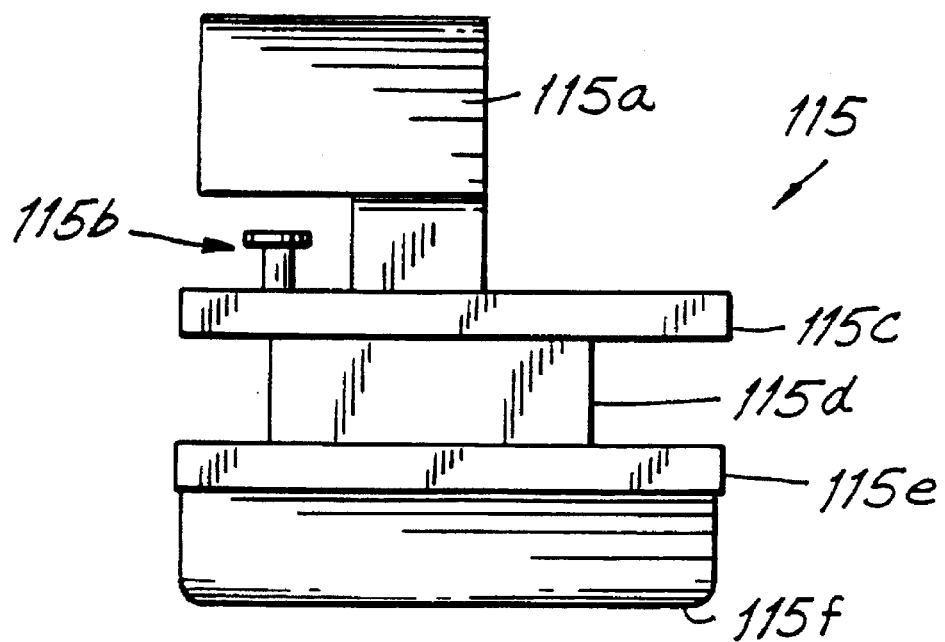
FIG. 12 illustrates a front view of the pusher slide.

Referring additionally now to FIGS. 11 and 12, resilient stop spring 116 has an elongated distal end with flap 116a for mounting into slot 102f in the right frame 102R. Spring 116 has a bend 116e, and a proximal end divided into a pusher bar stop latch 116c which provides means for locking the rear pusher bar 108 and a camming surface 116b which is angled by bend 116f, as illustrated. Slide member 115 has a cam member 115a, an anchor post 115b for engaging the distal hook end of spring 117, an upper base 115c, a connecting portion 115d, a lower base, 115e, and a curved pushing surface 115f. Slide member 115 rides along the longitudinal access aperture 102g and is mounted in the frame 102 such that the upper base is in the enclosed interior space of the frame 102, and the lower base 115e and pushing surface 115f project outside of the frame. The cam member 115a is engagable with the camming surface 116b of the spring 116. Upon moving distally the cam member 115a pushes spring 116 downward, thereby pivoting the stop latch 116c into a non-engagable position below the stopping edge 108g of the rear pusher 108.

Spring 117 is connected by a distal hook to the anchor post 115b and by a proximal hook to the pin 118, which is received into aperture 102m in right frame portion 102R.

Figure 13A:
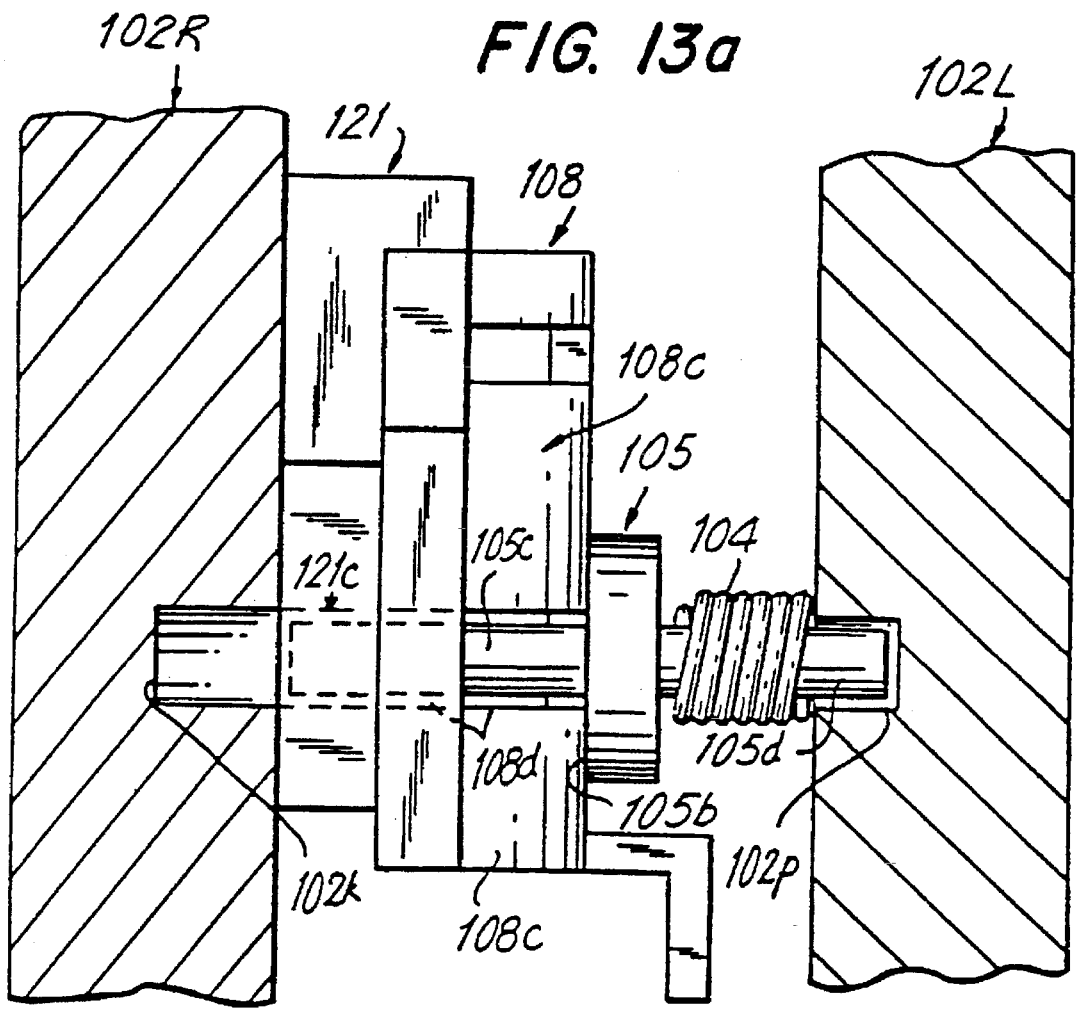
FIGS. 13a and 13b illustrate a front view of the channel lock pin in the unlocked and locked positions, respectively.
Figure 14:
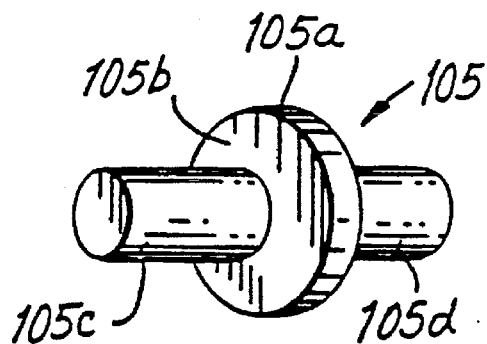
FIG. 14 illustrates the channel lock pin in perspective view.
Figure 13B:
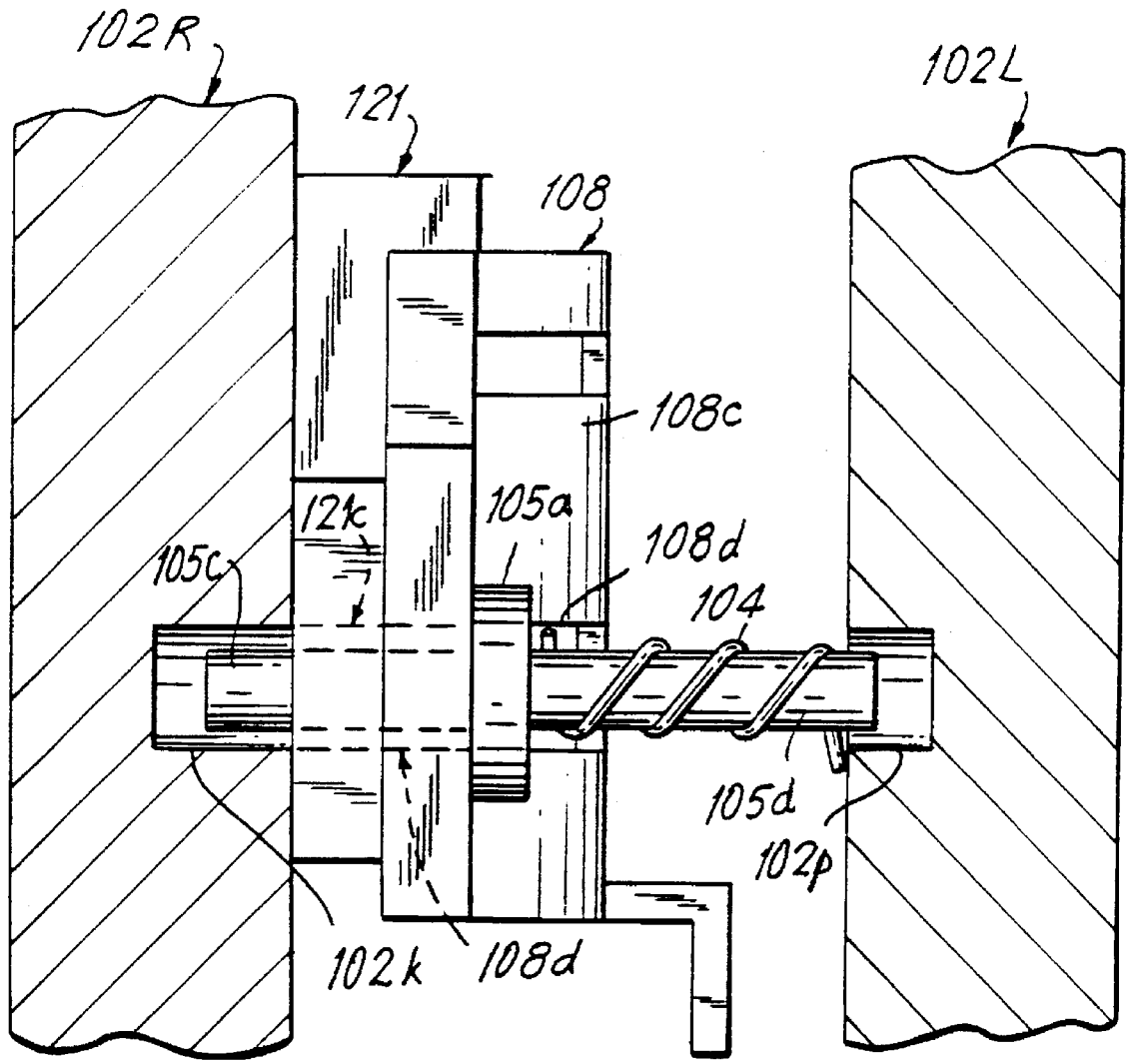

Referring additionally now to FIGS. 13a, 13b and 14, channel lock pin 105 provides means for locking the rear channel 121 and comprises a cylindrical portion 105a with camming surface 108b, and an axial shaft portion having ends 105c and 105d. When in the non-locking position channel lock pin 105 is located as illustrated in FIG. 13a. End 105d of the shaft is disposed axially through spring 104 and into hole 102p in the left frame portion 102L. End 105c is disposed through slot 108d of the rear pusher bar 108. When channel 105 is in the locking position as shown in FIG. 13b end 105c is disposed through aperture 121c in the rear channel 121, and hole 102k in the right frame portion 102R.

FIG. 15 illustrates the first transmission means (for transmitting linear movement to the clip advancing means) comprising the rear pusher bar 108, rear pusher bar tube 125, and front pusher bar tube 126, and the second transmission means comprising the rear channel 121, rear channel tube 123, and front channel tube 129. The rear channel 121 is connected to rear channel tube 123 by means of screw 122 disposed through aperture 121a. As can be seen additionally from FIG. 16, rear channel tube 123 has a proximal projection 123b having an aperture 123a for receiving screw 122. Rear channel tube 123 provides means for transferring linear movement from the rear channel 121 to the front channel tube 129 and is generally cylindrical in shape having a hollow bore and an external circumferential notch 123c for enabling the front channel tube to rotate.

Rear channel tube 123 is slidably mounted within the bore of front channel tube 129 which provides means for transferring linear motion from rear channel tube 123 to the front channel 133. Front channel tube 129 has a distal projection 129b having an aperture 129a for receiving screw 130 which is the mounting means for the front channel 133. Front channel tube is slidably mounted within the distal cylindrical chamber 102a of frame 102. Aperture 129a in the front channel tube 129 receives pin 128 which projects into groove 123c in the rear channel tube 123.

Rear pusher bar 108 is connected to the proximal projection 125b of the rear pusher bar tube 125 by means of pin 124 disposed through apertures 108a in the rear pusher bar 108 and 125a in the rear pusher bar tube 125. Rear pusher bar tube 125 provides means for transferring linear movement from the rear pusher bar 108 to the front pusher bar tube 126 while permitting the front pusher bar tube 126 to rotate. Rear pusher bar tube 125 is generally of cylindrical shape and has an external circumferential notch 125c for engaging proximal thrust collar 126b in the front pusher bar tube 126. Front pusher bar tube 126 has a distal projection 126c having an aperture 126a for receiving screw 127. Screw 127 is for mounting the proximal end of front pusher bar 143 and is disposed through aperture 143a in the front pusher bar.

Front pusher bar tube 126 transfers linear movement to pusher bar 143 from rear pusher bar tube 125. Cooperating thrust collar 126b and cylindrical notch 125c provide means for allowing rotation of front pusher bar tube 126 relative to rear pusher bar tube 125.

Rear pusher bar 108, rear pusher bar tube 125, front pusher bar tube 126, rear channel 121, front channel tube 129, and rear channel tube 123 are all slidable in the longitudinal direction. When the instrument 100 is actuated rear pusher bar 108, pusher bar tube 125 and front pusher bar tube 126 move proximally as indicated by arrow "P", and the rear channel 121, rear channel tube 123, and front channel tube 129 move distally as indicated by arrow "D". In addition to longitudinal movement, front pusher bar tube 126 and front channel tube 129 are rotatable around the instrument axis.

Figure 17:
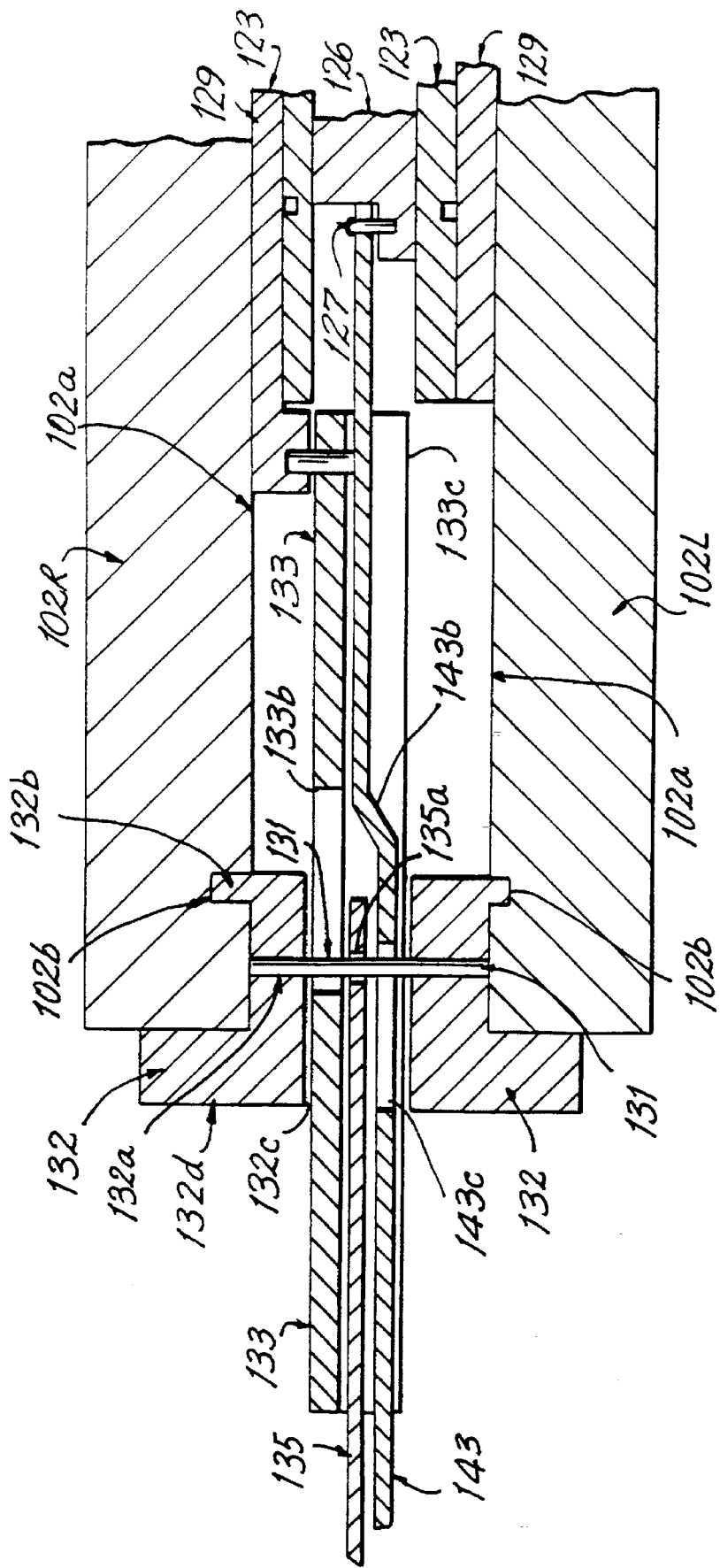
FIG. 17 illustrates a sectional top view of the collar fitting.

Referring additionally now to FIG. 17, collar is generally cylindrical in shape having a radial aperture 132a, for receiving pin 131; a circumferential detent 132b for mounting into circumferential groove 102b in the frame; a rectangular slot 132c for receiving front channel 133, jaw blade 135, and front pusher bar 143; and a distal portion 132d which is located exterior to the frame. Collar 132 is rotatable but does not move longitudinally. The proximal end of front channel 133 is mounted to the front channel tube 129 by means of screw 130 disposed through apertures 133a and 129a. Front channel 133 has a slot 133b to allow longitudinal movement without interference from pin 131. When the instrument 100 is actuated, by pressing handle 112, front channel 133 moves distally. Slot 133b must therefore extend longitudinal for a distance sufficient to permit full distal movement of the front channel 133.

Front channel 133, which provides means for closing jaws 135b, also has upper and lower guide rails 133c which project transversely from the top and bottom of front channel 133, and which extend longitudinally. Guide rails 133c serve as means to retain and align front pusher bar 143 and jaw blade 135 as well as means to close jaws 135b.

Front pusher bar 143 is connected to the front pusher bar tube 126 by means of screw 127 disposed through apertures 143a and 126a. Front pusher bar 143 has a bend 143b to widen the distance between it and the front channel 133 so as to accommodate jaw blade 135 disposed therebetween. Front pusher bar 143 has a slot 143c to allow longitudinal movement without interference from pin 131. When the instrument is actuated by pressing handle 112, front pusher bar 133 moves proximally. Slot 143c must therefore extend longitudinally for a distance sufficient to permit full proximal movement of the front pusher bar 143.

Jaw blade 135 has an aperture 135a for receiving pin 131 and has a proximal end disposed within cylindrical collar 132. Jaw blade 135 provides clip closing means.

Figure 16:
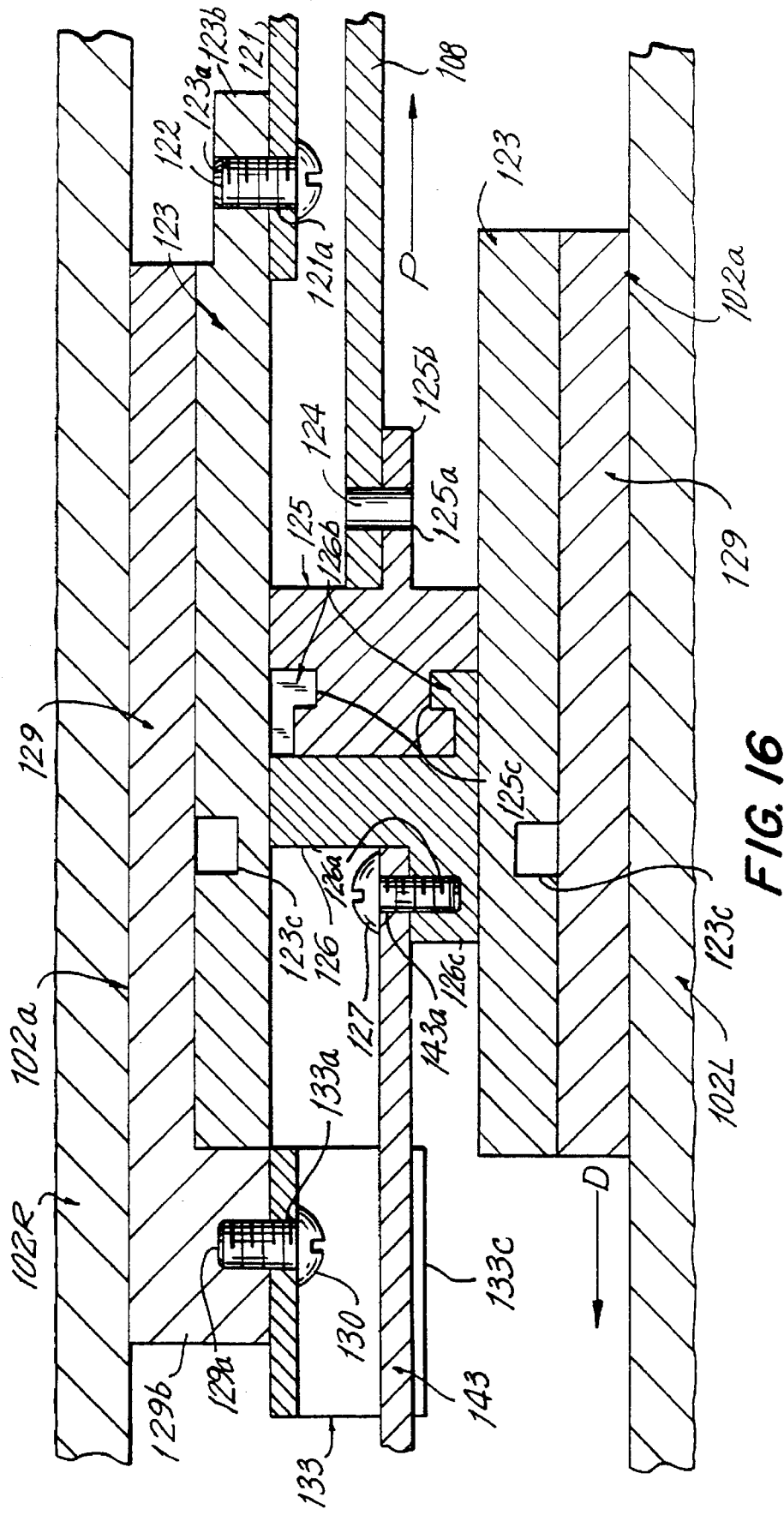
FIG. 16 illustrates a sectional top view of the transmission coupling.

As can be seen from FIGS. 15, 16 and 17, when collar 132 is rotated for example by manually turning the distal portion 132d, jaw blade 135, front channel 133, and front pusher bar 143 are likewise rotated, as well as front tube channel 129 and front pusher bar tube 126. Unlike front pusher bar 143 and front channel 133, jaw blade 135 does not also move longitudinally.

Figure 18:
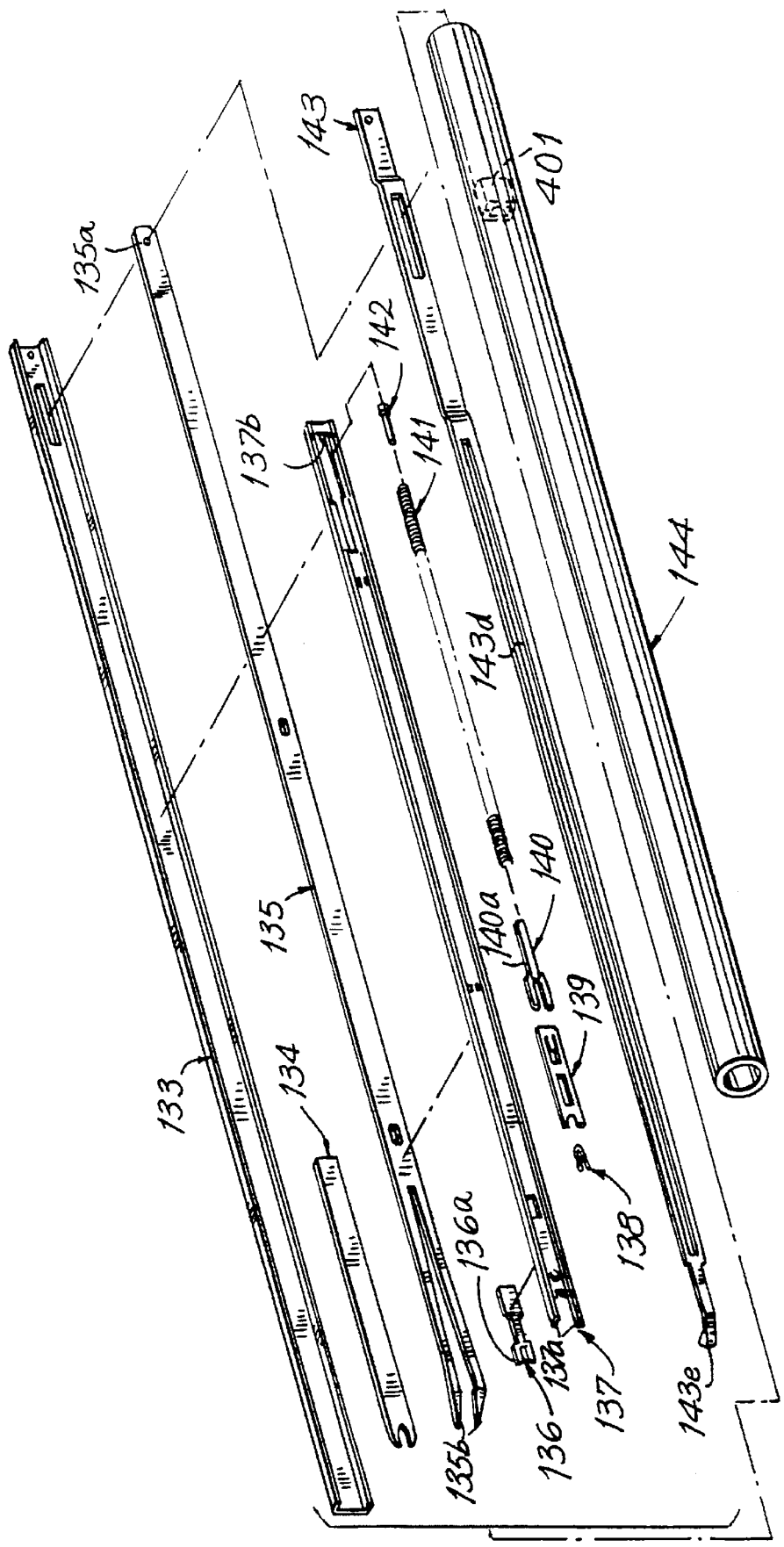
FIG. 18 illustrates an exploded perspective view of the endoscopic portion of the instrument.

Referring now to FIG. 18, the endoscopic portion of the instrument comprises a cover tube 144 enclosing front pusher bar 143, spring anchor shaft 142, spring 141, rear pusher clip 140, front pusher clip 139, (optional) clips 138, clip carrier 137, safety stop 136, jaw blade 135, tissue stop 134, front channel 133, and sealing block 401.

Cover 144 is an elongated tube fixed at its proximal end to collar 132. Front pusher bar 143 is an elongated piece longitudinally disposed within cover 144. In addition to features discussed above, front pusher bar 143 comprises an elongated longitudinal slot 143d, and inclined pusher tip 143e. Carrier 137 is longitudinally positioned along the side of pusher 143 and provides a means for carrying surgical clips 138 which are disposed within the longitudinal guide rail 137a. At its proximal end carrier 137 has a mounting post 137b for spring anchor shaft 142. The proximal end of spring 141 is mounted on anchor shaft 142, and the distal end of spring 141 is mounted to the proximal end of rear pusher clip 140. Rear pusher clip 140 has a bar 140a which rides in slot 143d of the front pusher bar. The distal end of the rear pusher clip 140 contacts the proximal end of the front pusher clip 139, which engages and pushes the clips 138 distally.

Safety stop 136 is an escapement with prong members 136a which project into the path of the clips 138 to limit the distal loading of the clips to one clip at a time. Safety stop 136 is attached to the distal end of carrier 137.

Jaw blade 135 is disposed within the front channel 133 and has a pronged distal end with jaws 135b which are flexibly movable toward each other. When the instrument is actuated the jaws are forced together by the camming action of the guide rails 133c of the distally moving front channel 133. Tissue stop 134, which is fixed to the side of the jaw blade 135 prevents the blood vessel or other tissue from proximally moving beyond the jaws 135b.

Figure 19A:
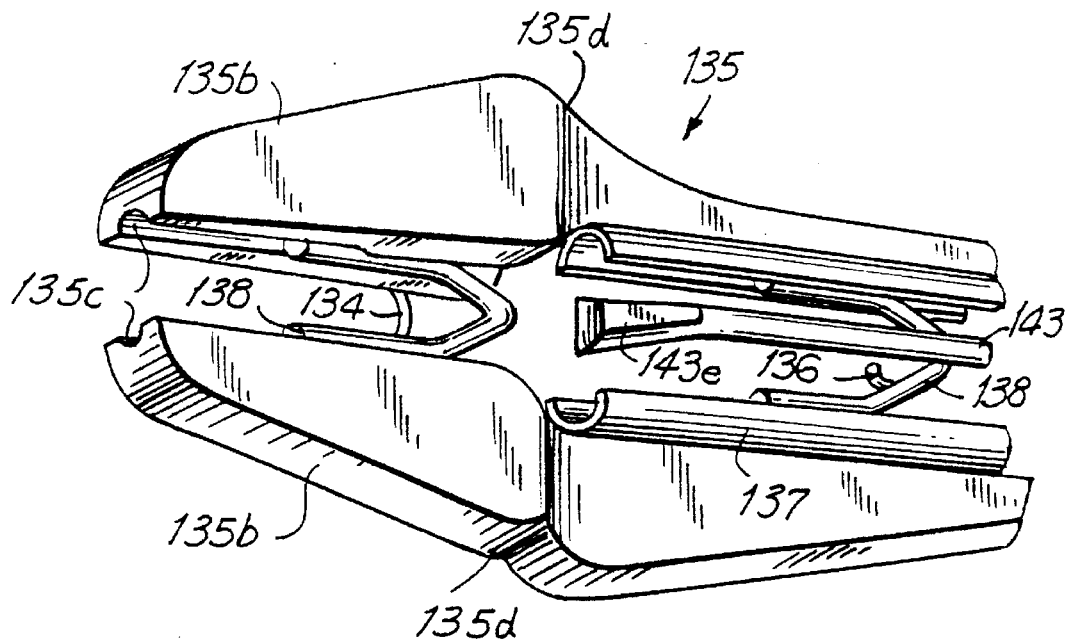
FIGS. 19a and 19b illustrate in perspective view the closing of the jaw blade to apply a surgical clip.
Figure 19B:
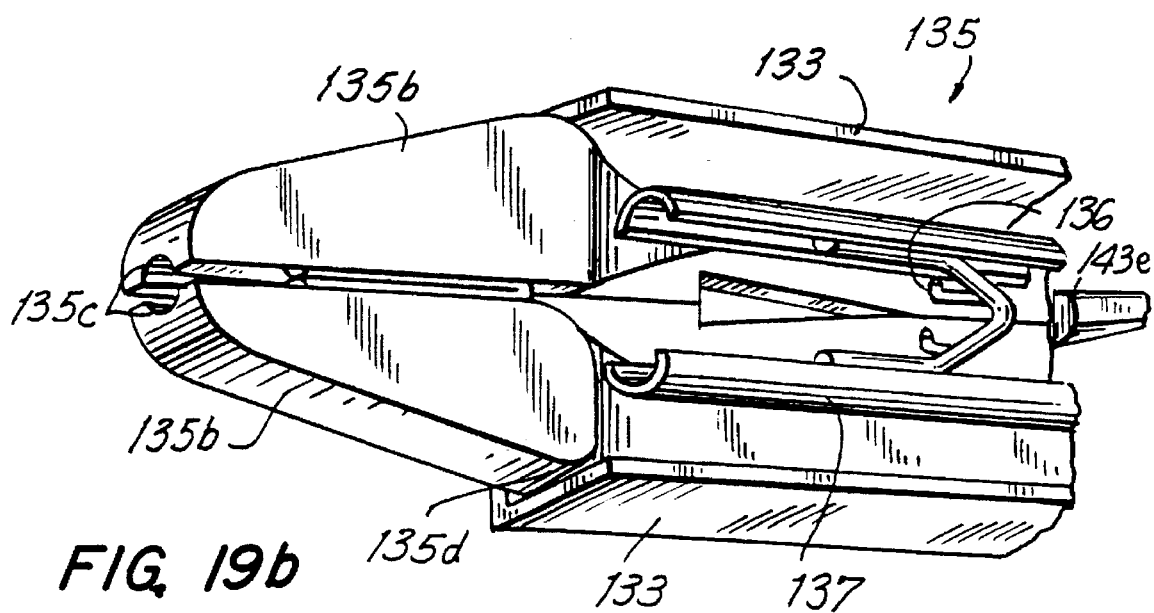

FIGS. 19a and 19b illustrate a clip located between jaws 135b. Grooves 135c facilitate the proper alignment and positioning of the clip. Jaws 135b also have camming surfaces 135d which are contacted by the distally moving guide rails 133c thereby forcing the jaws (and the clip 138) into closed position. The jaws blade 135 does not move longitudinally.

When handle 112 is pressed, it pivots clockwise thereby pivoting levers 110 and 113, and link 109 (which pivots counterclockwise) and link 114 (which pivots clockwise).

Link 109 pushes the rear pusher bar 108 longitudinally in the proximal direction, and link 114 pushes the rear channel 121 longitudinally in the distal direction. Rear pusher bar 108 pulls the front pusher bar in the proximal direction via rear and front pusher bar tubes 125 and 126 respectively. The front and rear pusher bar tubes 126 and 125 are coupled so as to permit rotation of the front pusher bar tube 126 relative to the rear pusher bar tube 125. The rear channel 121 pushes channel 133 distally via rear channel tube 123 and front channel tube 129. The front and rear channel tubes 129 and 123 are coupled so as to permit rotation of the front channel tube 129 relative to the rear channel tube 123. When channel 133 advances distally, it cams the jaws of jaw blade 135 into the closed position, thereby closing a surgical clip.

As the rear pusher bar 108 is being pushed proximally to the rear of the instrument, offset flap 108e rides over the stop latch portion 116c of spring 116, and when the offset flap passes proximally beyond the latch 116c, said latch 116c then springs upward and engages edge 108g of the rear pusher bar 108. The pusher bar is then locked and prevented from going distally forward. Furthermore, when the rear pusher bar is moved to a proximal position, channel lock pin is permitted to extend further towards 102R. When the handle 112 is subsequently released, the rear channel 121 is allowed to return proximally to its original prefiring position. When it does so, aperture 121c becomes aligned with aperture 102k in the right frame 102R, and the lock pin slides therethrough, locking the actuating mechanism so that the handle cannot be pressed again. The reason for this safety locking mechanism is that, having already closed a clip 138, jaws 135b are not yet chambered with another clip. As a precautionary measure, lock pin 105 prevents the operating surgeon from mistakenly closing the jaws when they are empty.

To release the lock mechanism, the surgeon pushes the exposed pushing surface 115f of the slide member 115 forward in the distal direction. Cam member 115a then presses down the camming surface 116b of spring 116. This pushes down latch 116 and disengages the rear pusher bar 108, which slides forward. When rear pusher bar 108 slides forward the inclined camming surface 108c wedges the lock pin 105 out of engagement with apertures 102k and 121c, thereby unlocking the actuation mechanism, Furthermore, as rear pusher bar 108 springs forward the front pusher bar 143 also moves forward and pushes another clip 138 into position between jaws 135b. The instrument 100 may then be reactuated to apply another clip.

A feature of this invention is that the transmission system transmits linear, longitudinal motion to the endoscopic portion of the instrument, while allowing the endoscopic portion of the instrument to rotate relative to the frame and actuating mechanism. This is accomplished by means of the couplings between front and rear pusher bar tubes 126 and 125, between front channel tube and rear channel tube 129 and 123, and between the collar 132 and the frame 102.

In the above described embodiment the endoscopic portion is not detachable. However, an alternative embodiment of the present invention comprises a disposable and replaceable endoscopic portion which is detachable from a reusable frame.

Figure 20:
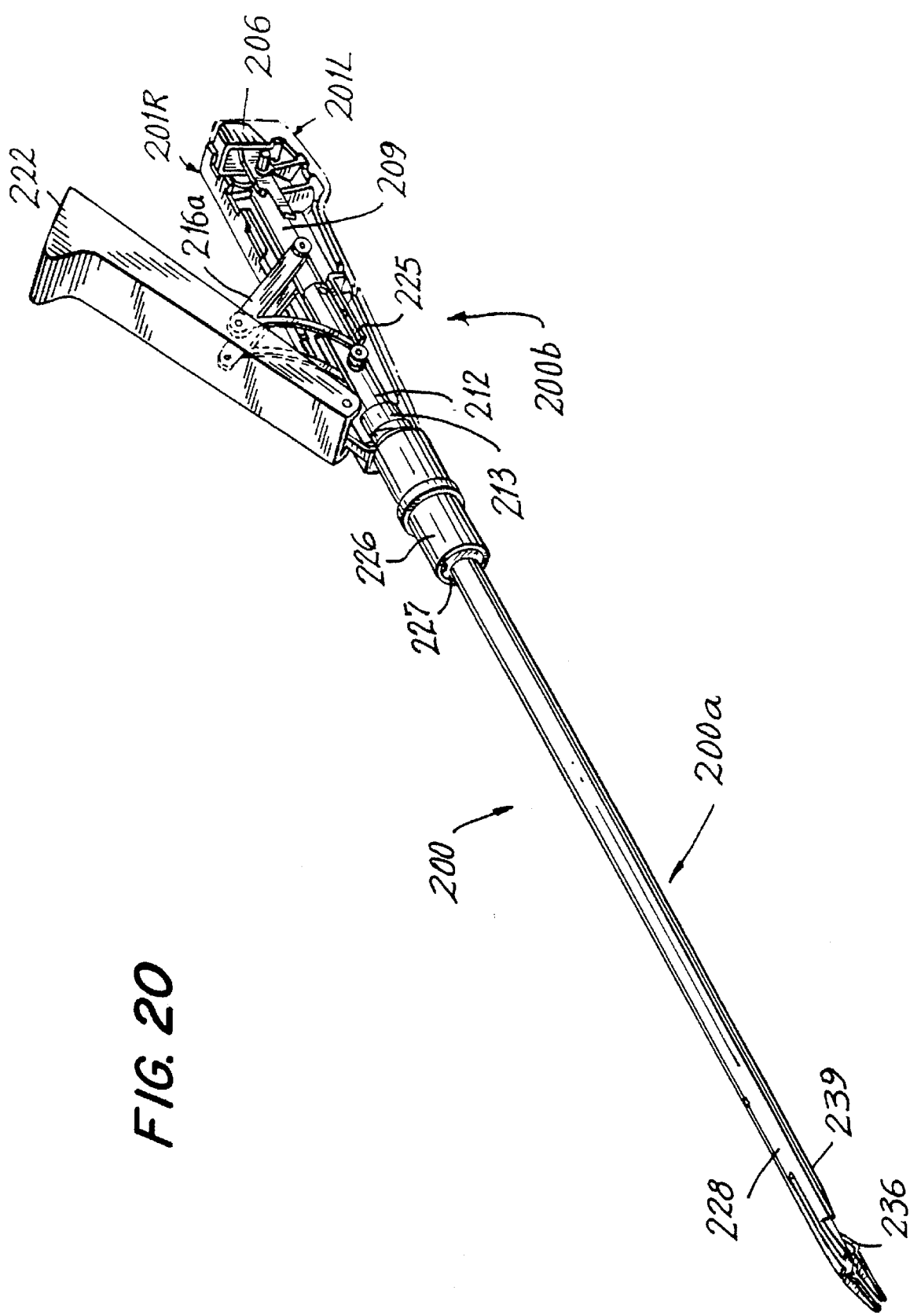
FIG. 20 illustrates a cut away perspective view of an alternative embodiment of the present invention.

FIG. 20 shows a cutaway perspective view of the alternative embodiment of the present invention 200 which generally comprises a reusable actuating body 200b supporting replaceable and disposable endoscopic portion 200a. Included are means for actuating the instrument, transmission means, means for applying a surgical clip to a blood vessel or the like, means for locking the instrument, and means for repositioning another clip and unlocking the mechanism.

Figure 21:
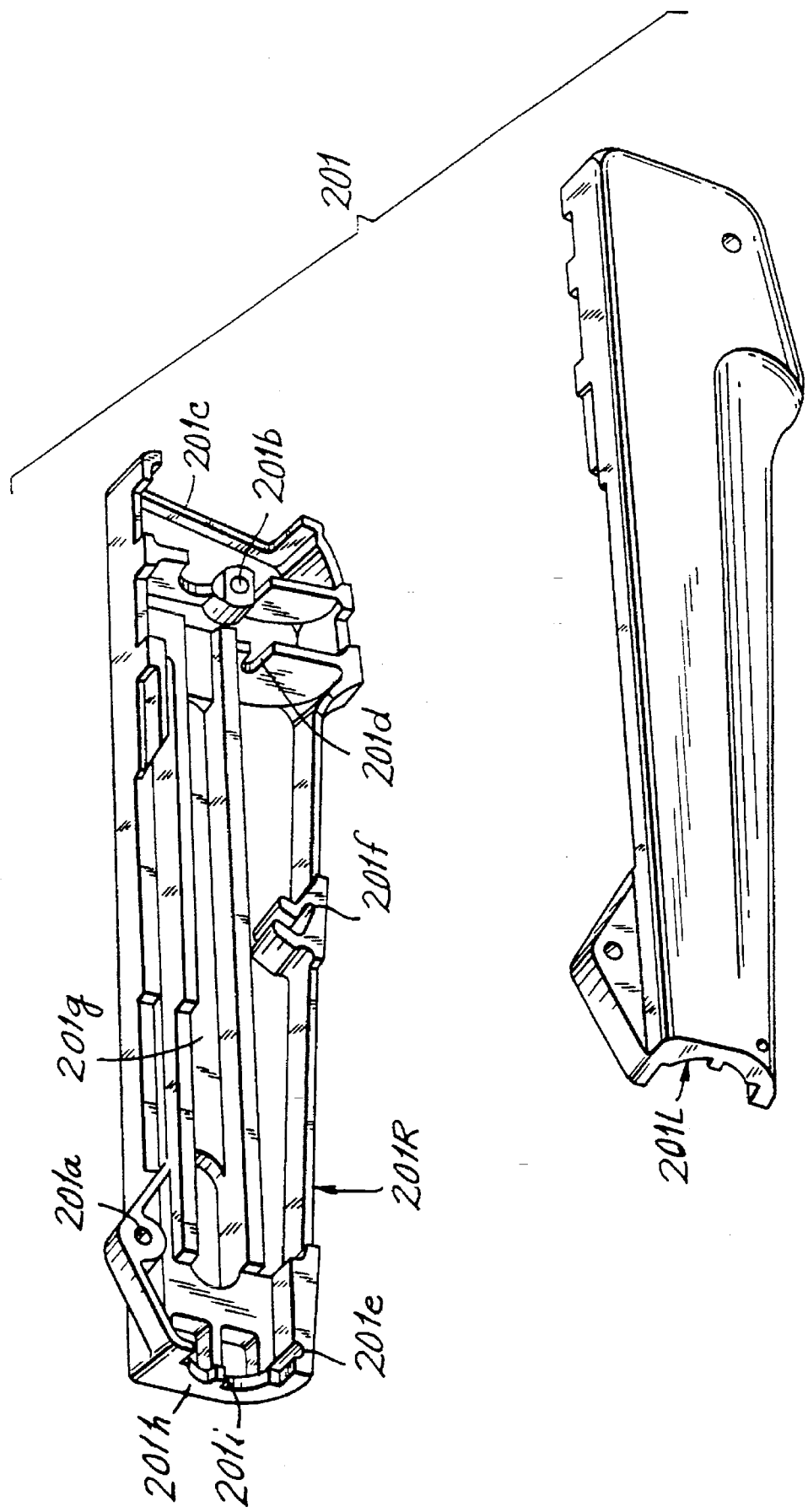
FIG. 21 illustrates the frame of an alternative embodiment.
Figure 22:
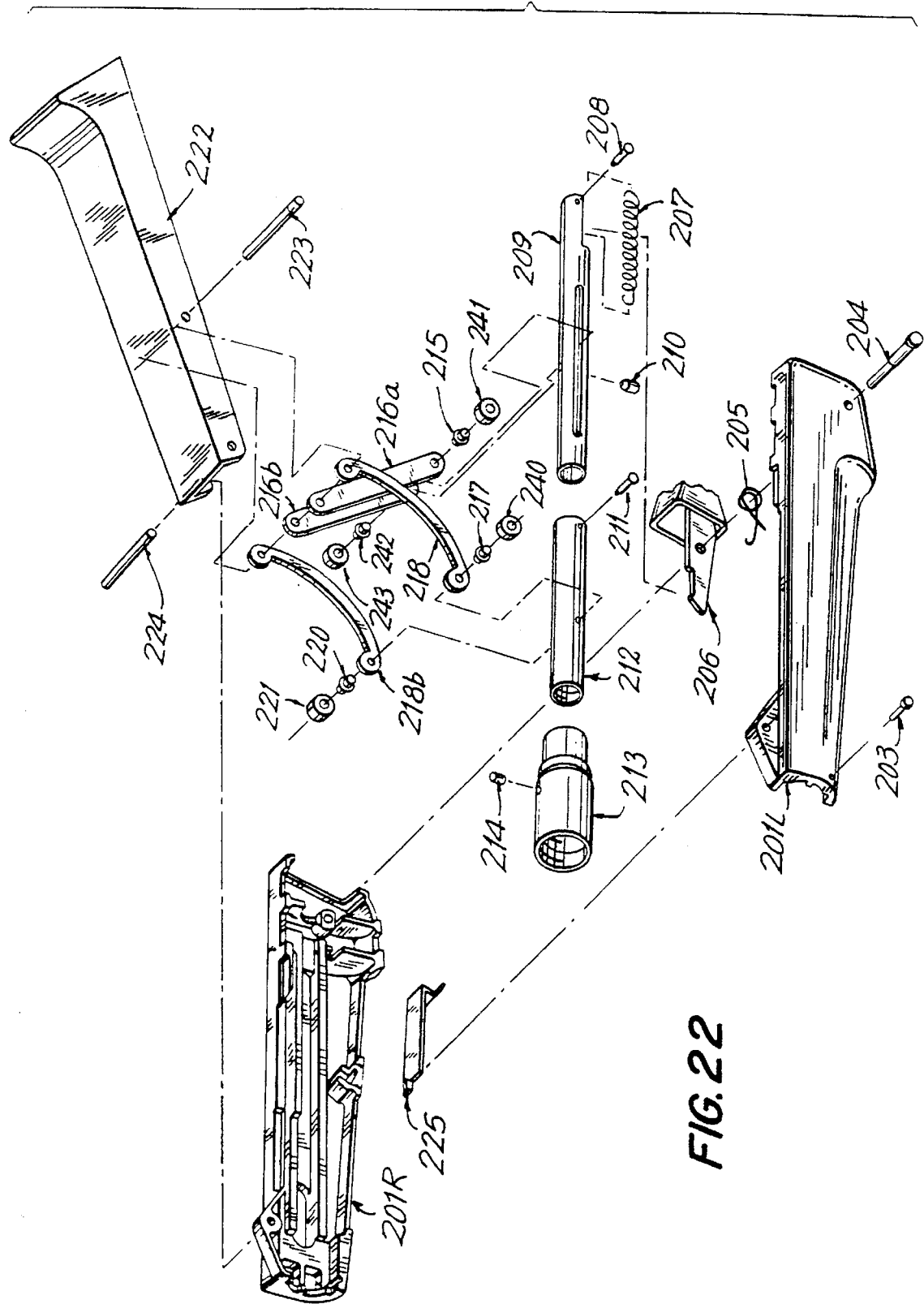
FIG. 22 illustrates an exploded perspective view of the actuating and transmission system of an alternative embodiment.
Figure 23:
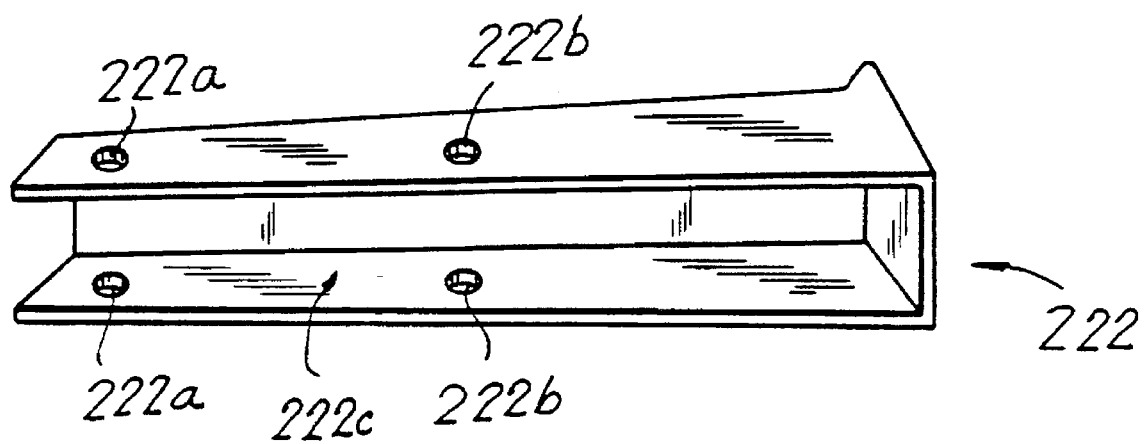
FIG. 23 illustrates the handle of an alternative embodiment.
Figure 25:
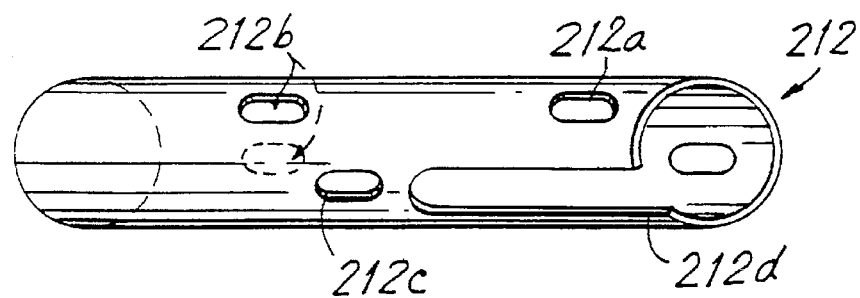
FIGS. 25 and 25a illustrate the channel tube of an alternative embodiment in perspective and side sectional views, respectively.
Figure 26:
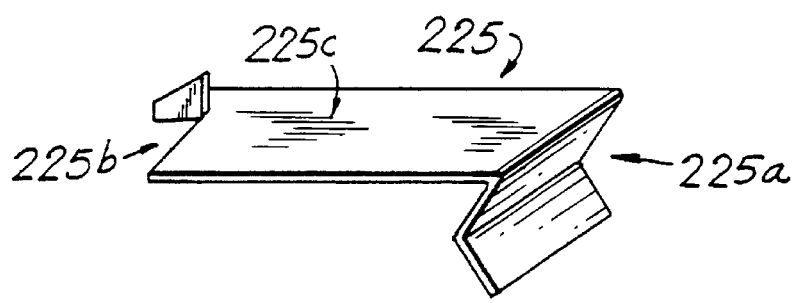
FIG. 26 illustrates the leaf spring of an alternative embodiment.
Figure 27:
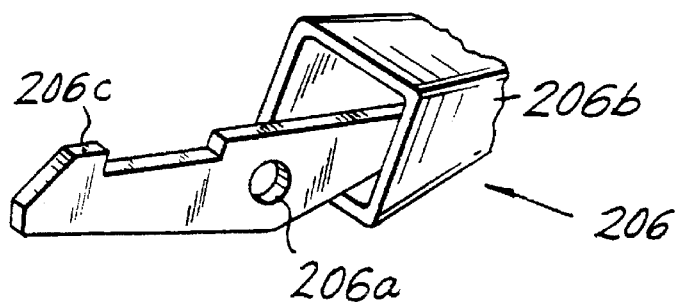
FIG. 27 illustrates the release button of an alternative embodiment.
Figure 25A:
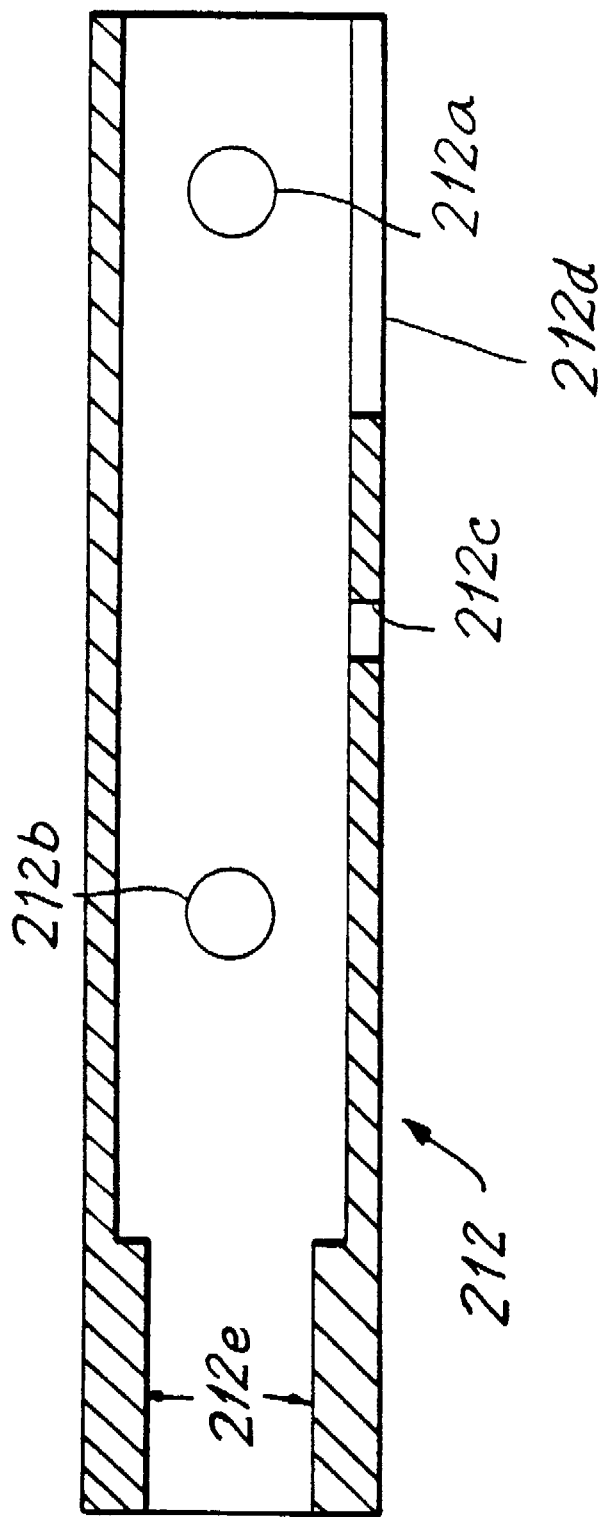

More particularly, referring to FIGS. 20, 21 and 22, frame 201 comprises a left frame portion 201L and right frame portion 201R. These portions may be either cast or machined pieces of polymeric resin or metal. The left and right portions may optionally be fastened together by means of fastening screws although rivets, welds, adhesives, or other means of joining the frame portions may be used. Frame 201 is elongated and is of overall size and shape convenient for being held in the hand. Frame 201 has an interior surface defining a distal opening 201b, a proximal opening 201c, an interior transmission guideway 201g, apertures 201a and 201b for receiving pins 224 and 204 respectively, backstop notch 201d for spring 205, bottom notch 201e, mounting notch for spring 225, and distal opening detents 201i.

Referring additionally to FIGS. 23, 24a, 24b, 25a, 26 and 27, handle 222 is an elongated piece which is pivotably mounted to the distal end of frame 201 by means of pin 224 which is disposed through aperture 222a in the handle and 201a in the frame. Aperture 222b is adapted to receive link pivot pin 223. Elongated cavity 222c is adapted to receive pusher links 216 and 216a, and channel links 218 and 219.

Channel links 218a and 218b preferably are curved elongated pieces having upper apertures for receiving pin 223, and lower apertures for receiving pins 217 and 220 respectively. Channel links 218a and 218b provide means for transferring movement from the handle 222 to the channel tube 212, and act as a load limiter as well.

Pusher links 216a and 216b are elongated pieces having apertures for receiving pin 223 and apertures for receiving pins 215 and 242 respectively. Pusher links 216a and 216b provide means for transferring movement from the handle 222 to the pusher tube 209.

Pins 215, 217, 220 and 242 each comprise a disc like center portion, and two shafts projecting axially therefrom. The inwardly projecting shaft is adapted to be received into the respective aperture of the channel or pusher link, and the oppositely projecting shaft is adapted to be received into the axial bore of the respective roller bearings 241, 240, 221, and 243. The inwardly projecting shafts of pins 217 and 220 are received into apertures in the channel tube 212, whereas the inwardly projecting shafts of pins 215 and 242 are disposed through the side slots of the pusher tube 209.

The roller bearings 240, 221, 241, 243 are adapted to slide along the guideways 201g in frame 201.

Pusher tube 209 provides a first transmission means for transmitting linear movement to the pusher bar 229 and comprises an elongated tubular piece located within the transmission guideway 201g. At its proximal end pusher tube 209 has apertures 209a for receiving cross pin 208, and proximal terminal notch 209b. Pusher tube 209 also comprises a bottom slot 209c for engaging release button 206, an aperture 209d for receiving pusher tube camming pin 210, side slots 209e for receiving pins 215 and 242, and an interior circumferential projection 209f at the distal end of the pusher tube for engaging the proximal end of the pusher 229 (see below).

Channel tube 212 provides a second transmission means for transmitting linear movement to channel 238 and comprises a proximal aperture 212a for receiving pin 211, apertures 212b for receiving pins 217 and 220, bottom aperture 212c for engaging spring clip 225, and proximal slot 212d for receiving camming pin 210. Pusher tube 209 is slidably mounted within channel tube 212 and the two are biased into alignment by means of spring 207 which is axially disposed within pusher tube 209 and which is attached at its proximal end to pin 208 and at its distal end to pin 211. Channel tube 212 further has an interior circumferential projection 212e at the distal end of for engaging the proximal end of channel 233.

Leaf spring or spring clip 225 is a catch means for locking the channel tube in the proximal position after the instrument has been actuated. Spring clip 225 has a distal end with angled portion 225a for being mounted in notch 201f of the frame. At its distal end, resilient spring clip 225 has a catch 225b which is engagable with aperture 212c of the channel tube 212. Spring clip 223 has a camming surface 225c which is contacted by pusher tube camming pin 210 when the pusher tube moves in the distal direction, thereby depressing the spring clip 225 and disengaging and unlocking the channel tube 212.

Release button 206 is pivotally mounted at the proximal end of frame 201 by means of pivot pin 204 which is disposed through aperture 206a and 201b. Release button 206 has a proximal end 206b which projects through aperture 201c in the frame, and a catch 206c at its distal end for engaging aperture 209c of the pusher tube 209.

Figure 28:
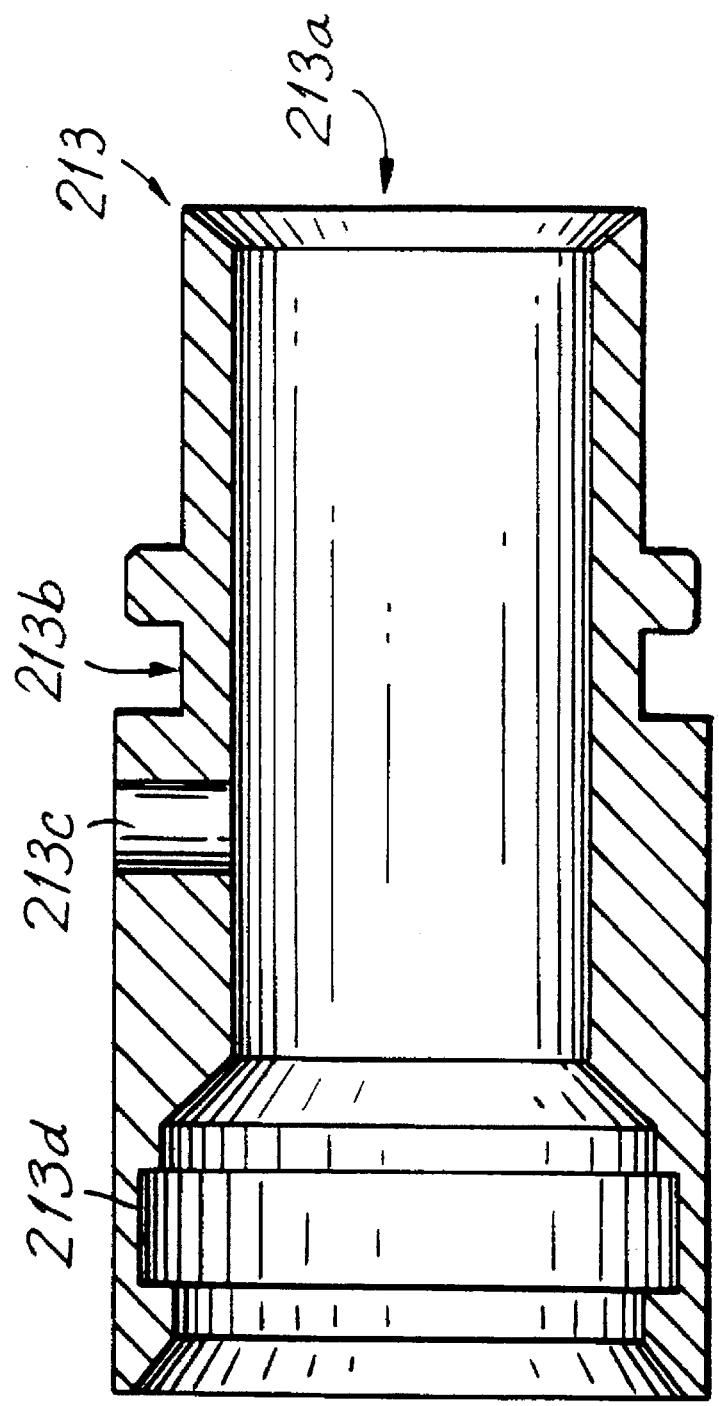
FIG. 28 illustrates a sectional side view of the outer tube of an alternative embodiment.

Referring additionally now to FIG. 28, outer tube 213 is adapted to be received into distal access opening 201b of the frame. Outer tube 213 has a proximal opening 213a, a circumferential outer notch 213b which is adapted to receive detent 201i in the distal opening of the frame, an aperture 213c for receiving pin 214, and a circumferential inner notch 213d at the distal end of the outer tube for engaging and interlocking with the collet 227.

Pin 214 is received into aperture 213c of the outer tube and projects a small distance beyond the outer surface thereof. It provides a contact surface to engage the interior notches of the sleeve 226 as discussed below.

The above described portion of the alternative embodiment is the reusable portion 200b. The replaceable endoscopic portion 200a described below is adapted to be received into the distal end of the reusable portion 200b and to project outwardly therefrom. The endoscopic portion 200a is rotatable relative to the reusable portion 200b.

Figure 29:
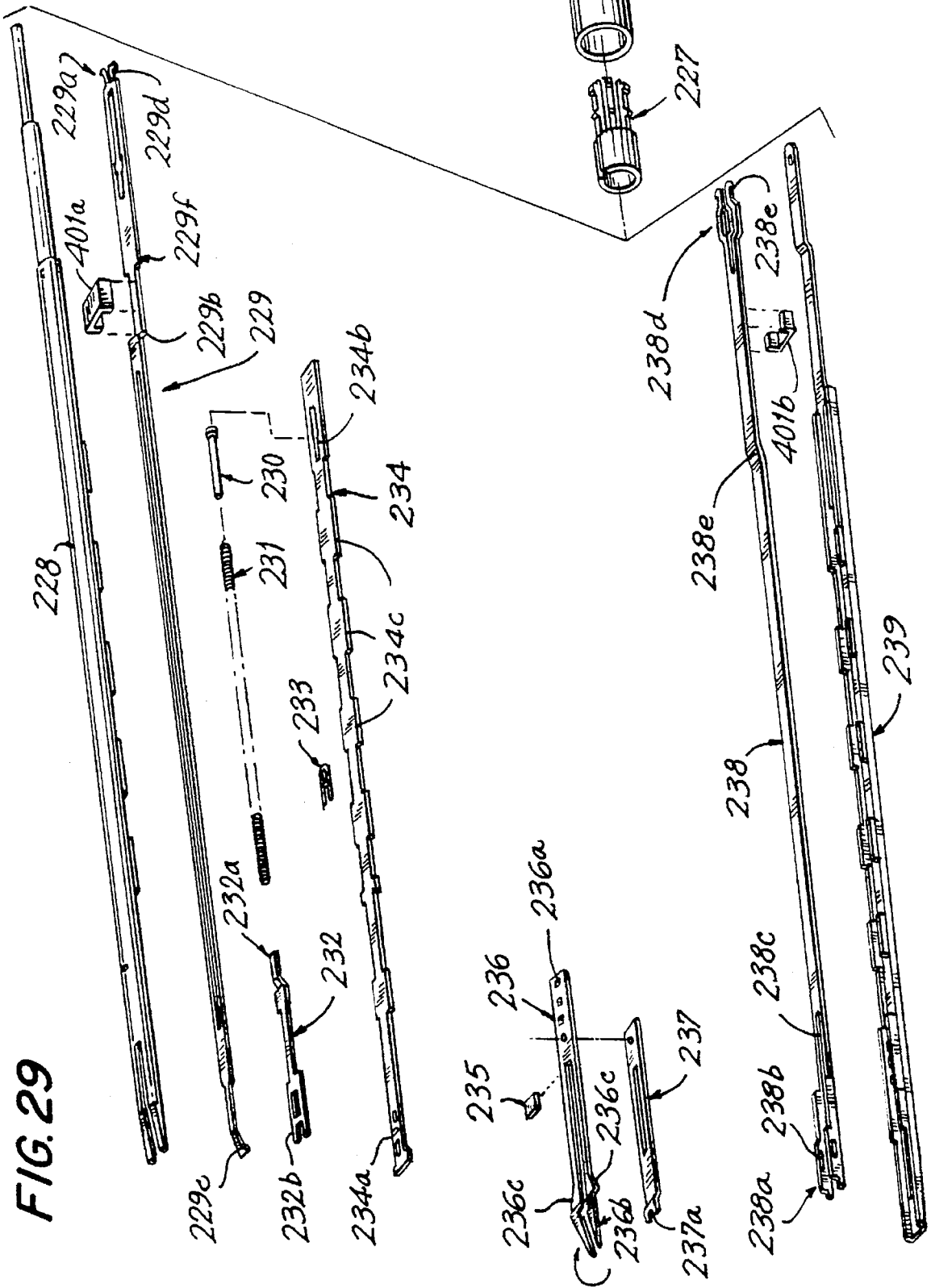
FIG. 29 illustrates in exploded view the endoscopic portion of an alternative embodiment.
Figure 30:
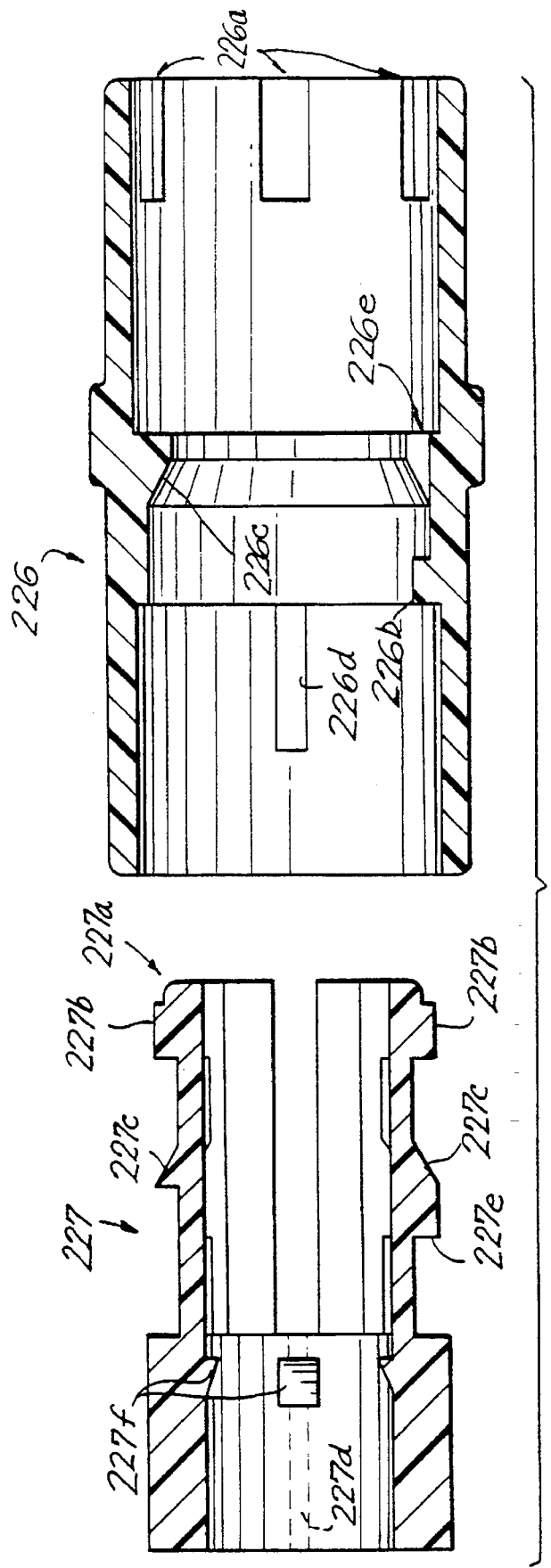
FIG. 30 illustrates a sectional top view of the collet and sleeve of an alternative embodiment.

Referring additionally now to FIGS. 29 and 30, the replaceable portion 200a includes a coupling which comprises sleeve 226 and collet 227. The coupling is adapted to connect the endoscopic portion to the non-endoscopic instrument body portion while permitting rotation of the endoscopic portion. Sleeve 226 is a tubular piece having several longitudinal notches 226a on the interior surface of the proximal end for engaging the protruding portion of pin 214. The pin 214 and notches 226a cooperate so as to form click-stop settings wherein the sleeve can rotate to any of several positions and be temporarily seated in the chosen position. Sleeve 226 has slot 226e and detent 226b which are adapted to cooperate with the collet 227 to retain the collet 227 within the sleeve 226 once the collet 227 has been inserted. Detent 226b serves as a backstop by abutting the distal surface of projection 227e in the collet. Key 226d on the inside surface of sleeve 226 is adapted to fit into longitudinal spline 227d in the outside surface of collet 227. Camming surface 226c is adapted to push against. surface 227c in the outer surface of the collet 227.

The proximal portion of collet 227 comprises several proximally extending prongs 227a, each prong having on its outer surface a projection 227b for engaging and locking into circumferential notch 213d on the interior surface of the outer tube 213. Once inserted into sleeve 226, collet 227 locks into place by means of projecting surface 227e which abuts detent 226b in the sleeve. Projections 227f lock into cooperating notches in the cartridge halves 228, 229. When camming surfaces 227c on the exterior surface of the prongs 227b are contacted by camming surface 227c in the sleeve as for example when the sleeve 226 and collet 227 are pushed together, the prongs 227b are biased closer to the axial center of the collet 227, thereby enabling them to disengage from the outer tube.

The endoscopic portion is axially disposed through the collet and sleeve, and connects to the actuating and transmission mechanisms described above. As can be seen from FIG. 29, the endoscopic portion comprises upper and lower cartridge portions 228 and 239, and disposed within the cartridge portions are pusher bar 229, clip pusher 232, clip feed spring 231, spring anchor shaft 230, bottom clip track 234, capture plate 235, jaw blade 236, tissue stop 237, channel 238, clip 233 and sealing block 401.

Figure 31:
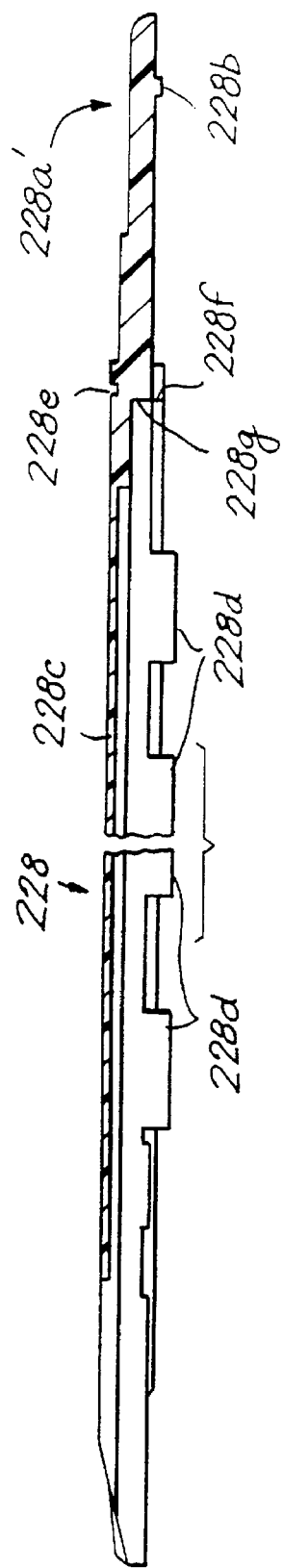
FIG. 31 illustrates a sectional side view of the upper portion of the cartridge of an alternative embodiment.
Figure 32:
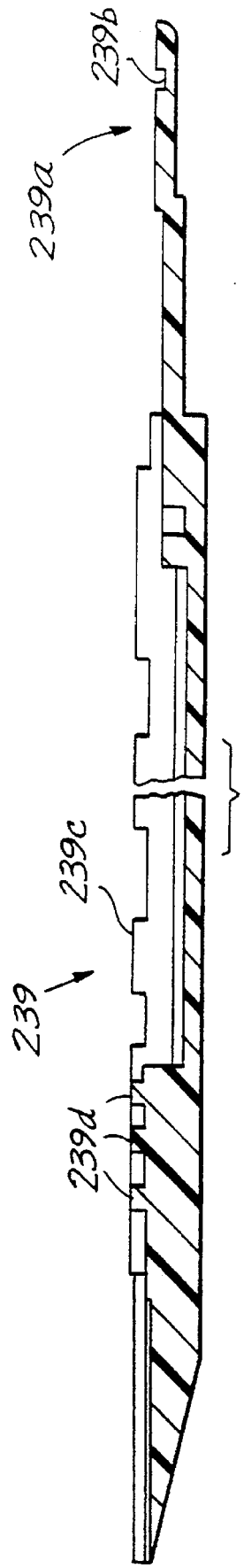
FIG. 32 illustrates a sectional side view of the lower portion of the cartridge of an alternative embodiment.

Referring additionally now to FIGS. 31 and 32, upper cartridge portion 228 comprises an elongated relatively small diameter piece which, in addition to lower cartridge portion 239, houses the endoscopic portion of the apparatus. The cartridge may be constructed of polymeric material suitable for surgical procedures and has a width of about 0.3 inches for practical use in endoscopic or laparoscopic surgical procedures. Upper cartridge portion 228 comprises a proximal end 228a having a projection 228b for engaging corresponding notch 239b in the lower cartridge portion, notches 228e for engaging corresponding projections 227f in the collet, stopping surface 228f for limiting the distal or forward movement of the pusher bar 229 by engaging projections 229f, stopping surface 228g for limiting the rearward or proximal movement of the pusher bar 229 by engaging bend 229b, rectangular projections 228d for alternating alignment with projections 239c in the lower cartridge portion 239, and guide way 228c for aligning the pusher bar 229.

Lower cartridge portion 239 comprises a proximal portion 239a having a notch 239b for receiving projection 228b, projections 239c, and projections 239d for engaging the corresponding apertures in the jaw blade 236.

Channel 238 is an elongated piece having a distal end with camming portions 238a for contacting the jaws 236b and pushing them into a closed position. Slots 238b are for receiving capture plate 235. Channel 238 has an aperture 238c for receiving projections 239d of the bottom portion of the cartridge 239, bend 238e, and proximal prongs 238d having notches 238e for engaging projection 212e in the channel tube. Prongs 238 are resiliently flexible towards each other. Tissue stop 237 has a distal end 237a to protect the blood vessel or other tissue from entering too far between the jaws 236b.

Jaw blade 236 has a proximal end with apertures 236a for engaging projections 239d in the cartridge thereby aligning and firmly seating the jaw blade 236. Jaws 236b at the distal end have camming surfaces 236c which are contacted by the camming surfaces 238a of the channel. When the channel moves in the distal direction the jaw blades 236b are cammed into the closed position, thereby closing a clip positioned within said jaws.

Bottom track 234 for clips 233 is an elongated flat piece having a distal end with projections 234a which serve as an escapement means to limit the feeding of clips 233 to one clip at a time. Bottom track 234 has a mounting post 234b for the spring anchor 230, and flat side projections 234a for fitting and alignment in the cartridge 228.

Clip pusher 232 has a distal end with prongs 232b adapted to fit around any distally push clips 233 forward. Clip pusher 232a has a proximal post 232a for mounting spring 231.

Spring 231 is axially mounted at its proximal end to anchor 230, and at its distal end to clip pusher 232. Spring 231 resiliently moves the clip pusher forward in the distal direction.

Pusher bar 229c provides a means for advancing the clips into the jaws. Distal end 229c pushes the clips forward one at a time from track 234 to a position between the jaws.

Pusher bar 229 has a bend 229b which abuts stopping surface 228g to limit the proximal movement of he pusher bar, projections 229f which abut stopping surface 228f for limiting distal movement of the pusher bar 229, and a proximal end with resilient prongs 229a, each prong having a notch 229d for engaging projection 209f in the pusher tube. The resiliency of the prongs allow them to bend inward sufficiently to enable them to snap into place when the endoscopic portion of the instrument is inserted into the reusable body.

Referring additionally now to FIG. 33a, which shows a top sectional view of the proximal coupling end of the endoscopic portion 200a, and to FIG. 33b which shows the same portion in side view, the cartridge portions 228 and 239 which house the endoscopic portion of the apparatus means, are disposed axially through the collet 227 and sleeve 226. As can be seen from the illustration pusher bar 229 and channel 238 are sandwiched between the cartridge portions, but have proximal ends 229a and 238d which, being slightly wider than the cartridge section 239a and 228a, protrude slightly from the sides. Inclined proximal edges of the pusher bar (229e) and the channel (238f) allow the respective prongs to be biased inward while the endoscopic portion 200a is being inserted into the reusable body 200b. The proximal portions 229a and 238a will then snap into place as channel tube projection 212e engages notches 238e and pusher tube projection 209f engages notches 229d, the prongs 229a and 238d thereupon resiliently expanding to their original position. The proximal movement of pusher tube 209 will draw the pusher bar 229 rearward in the proximal direction, and the distal movement of channel tube 212 will push the channel 238 forward.

Initially, the clip applier (both embodiments) is in the locked position, i.e., there is no clip loaded between the jaws. The jaws are biased open and are free to cam between the open and closed positions. This facilitates insertion of the endoscopic portion into an endoscopic tube or into the body since the jaws can cam partially closed, thereby avoiding interference with the positioning of the instrument.

When the clip applier has been properly positioned, the user may release the first and second transmission means from the locked position by pressing the release button (206). This disengages the first transmission means (pusher bar 209) which slides forward. The first transmission means comprises means to release the catch from the second transmission means. For example, in the first described embodiment the rear pusher bar has an inclined camming surface 108c to push aside channel lock pin 105 which locks the second transmission means. In the alternative embodiment pusher tube 209 (the first transmission means) has a depending pin 210 which, upon being carried forward, depresses leaf spring 225, thereby releasing the catch 225b from the channel tube 212 (second transmission means).

The first transmission means of both embodiments transfers motion to the pusher bar (143 and 229) which has a distal pusher end located behind the distal most clip in the array. When the pusher bar (i.e., the clip advancing means) moves forward the distal most clip is advanced to the jaws.

The second transmission means, upon being released, returns backward, thereby pulling the channel (113 in the first described embodiment; 238 in the alternative embodiment). The instrument is now ready to be actuated for clip application.

The endoscopic portion of the instrument 200a may be rotated relative to the reusable body 200b by manually turning sleeve 226.

As in the previously described first embodiment, the clip applier of the alternative embodiment is actuated by pressing the handle. When handle 201 is pressed pusher links 216a and 216b move pusher tube 209 proximally to the rear of the instrument thereby repositioning the pusher bar behind another clip, and channel links 218a and 218b move the channel tube 212 forward thereby causing the jaws to be closed for applying the surgical clip. The distally moving channel tube 212 pushes channel 233 forward, thereby camming the jaw blade 236 into a closed position for applying the surgical clip. The pusher tube 209 is locked in the proximal position when catch 206c of the release button 206 engages aperture 209c in the pusher tube. The channel tube 212 is locked in the proximal position when catch 225b of the leaf spring engages aperture 212c of the channel tube.

The instrument remains locked until the release button 206 is pressed, thereby unlocking the instrument as explained above.

FIGS. 34a and 34b illustrate the apparatus of the present invention in conjunction with the cannula 300, or endoscopic guide tube, of a trocar to apply a surgical clip to blood vessel 302. (Trocars generally comprise a cutting tip, cannula, and valve means for sealing the cannula). The trocar is used to penetrate the skin 301 of a patient and is inserted into the patient's body. Upon withdrawal of the cutting tip (not shown) of the trocar, the endoscopic portion of the apparatus 200a is inserted axially through the cannula 300 and maneuvered to the operating site where jaws 236b engage blood vessel 302. The endoscopic portion is in sealing engagement with the valve means to prevent entry or egress of gases.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical apparatus comprising:
   (a) a frame and at least one actuating handle movably mounted with respect to the frame;
   (b) an elongated section having a proximal end connected to the frame;
   (c) flexible opposing jaws positioned at the distal end of the elongated section;
   (d) a cam member having a proximal end which extends into the frame and a distal end which at least partially surrounds the flexible opposing jaws, the cam member being movably positioned within the elongated section between a proximal position and a distal position wherein the flexible opposing jaws are cammed into closure;
   (e) a pusher member having a proximal end which extends into the frame and a distal end, the pusher member being movably positioned within the elongated section between a proximal position and a distal position whereby a clip is moved within the flexible opposing jaws; and (f) a spring positioned within the frame and abutting the cam member and the pusher member, the spring biasing the cam member proximally and the pusher member distally.

2. The apparatus of claim 1, wherein said actuatina handle is operatively connected to said cam member and said pusher member within said frame such that movement of the actuating handle with respect to the frame moves the cam member and the pusher member against the bias of the spring.

3. The apparatus of claim 1, further comprising a first linkage mounted to the actuating handle and the pusher member, and a second linkage mounted to the actuating handle and the cam member.

4. The apparatus of claim 3, wherein the first linkage is configured to translate an arcuate movement of the actuating handle with respect to the frame into linear movement of the pusher member with respect to the frame, and the second linkage is configured to translate the arcuate movement of the actuating handle into linear movement of the cam member with respect to the frame.

5. The apparatus of claim 1, wherein the frame defines a stationary handgrip and wherein the actuating handle is movable between a first position spaced from the stationary handgrip and a second position in proximity to the stationary handgrip.

6. The apparatus of claim 5, wherein said actuating handle is operatively connected to said cam member and said pusher member within said frame such that movement of the actuating handle from the first position to the second position translates to movement of the cam member distally and the pusher member proximally relative to the frame.

7. The apparatus of claim 6 wherein the spring is a tension spring and movement of the actuating handle from the first position to the second position translates to stretching of the tension spring.

8. The apparatus of claim 1, wherein the pusher member includes a pusher tube movably positioned within the frame and the cam member includes a cam tube movably positioned within the frame, and the spring acts on the pusher tube and the cam tube, biasing the pusher tube distally and the cam tube proximally.

9. The apparatus of claim 1, wherein the elongated section defines a longitudinal axis and the elongated section is rotatable with respect to the frame, and further wherein, regardless of the angular orientation of the elongated section relative to the frame, the spring retains a angular orientation with respect to the frame.

10. The apparatus of claim 1, further comprising a seal block positioned within the elongated section and cooperating with the cam member and the pusher member to inhibit gas flow through the elongated section.

11. The apparatus of claim 1, further comprising a clip track mounted within the elongated section and a plurality of clips positioned within the clip track.

12. The apparatus of claim 1, further comprising (i) a latch positioned within the frame, the latch movable between a delatched position and a latched position wherein the latch engages the pusher member and restrains the pusher member in a proximal position against the bias of the spring, and (ii) a trigger mounted to the frame and movable from a first position to a second position to move the latch from the latched to the delatched position.

13. The apparatus of claim 1, wherein the pusher member includes a pusher bar and a pusher tube, and wherein the cam member includes a cam channel and a cam tube.

14. The apparatus of claim 1, further comprising a mechanism for detachably mounting the elongated section to the frame, a first part of the mechanism being positioned at the proximal end of the elongated section and a second part of the mechanism being positioned within the frame.

\* \* \* \* \*